(12) United States Patent
Rohrschneider et al.

(10) Patent No.: US 8,297,277 B2
(45) Date of Patent: Oct. 30, 2012

(54) DISPENSING DEVICE, STORAGE DEVICE AND METHOD FOR DISPENSING A FORMULATION

(75) Inventors: Marc Rohrschneider, Hagen (DE); Matthias Vehdelmann, Sundern (DE); Stephen T. Dunne, Stowmarket (GB)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 1417 days.

(21) Appl. No.: 11/565,293

(22) Filed: Nov. 30, 2006

(65) Prior Publication Data

US 2007/0163574 A1  Jul. 19, 2007

(30) Foreign Application Priority Data

Dec. 2, 2005 (EP) .................................... 05026286
Jan. 17, 2006 (EP) .................................... 06000866

(51) Int. Cl.
*A61M 16/00* (2006.01)
*A61M 15/00* (2006.01)
*A61M 11/00* (2006.01)
*B05D 7/14* (2006.01)

(52) U.S. Cl. .......... 128/203.21; 128/203.15; 128/200.14

(58) Field of Classification Search ............. 128/203.15, 128/203.19, 203.21, 200.14; 604/58; 222/92, 222/95; 206/528, 530, 533, 535, 538, 539, 206/828

See application file for complete search history.

(56) References Cited

U.S. PATENT DOCUMENTS

| | | | | |
|---|---|---|---|---|
| 4,522,622 A * | 6/1985 | Peery et al. | ................... | 604/191 |
| 4,627,432 A | 12/1986 | Newell et al. | | |
| 5,472,143 A * | 12/1995 | Bartels et al. | ................. | 239/462 |
| 5,896,855 A * | 4/1999 | Hobbs et al. | ............. | 128/203.15 |
| 6,092,522 A * | 7/2000 | Calvert et al. | ............ | 128/203.21 |
| 6,880,555 B1 | 4/2005 | Brunnberg et al. | | |
| 7,163,014 B2 * | 1/2007 | Nichols et al. | ........... | 128/203.26 |
| 7,219,665 B1 * | 5/2007 | Braithwaite | ............. | 128/203.21 |
| 2007/0151562 A1* | 7/2007 | Jones et al. | .............. | 128/203.21 |

FOREIGN PATENT DOCUMENTS

| | | | |
|---|---|---|---|
| WO | 2005/002654 A2 | 1/2005 | |
| WO | 2006/037636 A2 | 4/2006 | |

\* cited by examiner

*Primary Examiner* — Kristen Matter
(74) *Attorney, Agent, or Firm* — Roberts Mlotkowski Safran & Cole, P.C.

(57) ABSTRACT

A dispensing device, a storage device and a method for dispensing a medical formulation are proposed. Multiple doses of the formulation are stored in a carrier having multiple inserts, each insert containing a single dose. Preferably, each insert has at least one duct or nozzle for dispensing the respective dose. Each insert is located in a separate and sealed cavity in the carrier. The cavities can be individually opened for dispensing the respective dose from the respective insert.

26 Claims, 11 Drawing Sheets

DISPENSING DEVICE, STORAGE DEVICE AND METHOD FOR DISPENSING A FORMULATION

BACKGROUND OF THE INVENTION

1. Field of the Invention

The present invention relates to a dispensing device for dispensing a preferably medical formulation, in particular containing or consisting of a drug, as a spray including fine particles, wherein the dispensing device is adapted to receive or comprises a storage device with preferably multiple separate and pre-metered doses of the formulation to a storage device for a preferably medical formulation, and to a method for dispensing a preferably medical formulation, in particular containing or consisting of a drug or mixture of drugs, as a spray including fine particles from a storage device having multiple separate and pre-metered doses of the formulation.

2. Description of Related Art

Drugs delivered through dispensing devices, in particular inhalers, are intended to optimally target specific sites in the pulmonary system. These sites include the nasal passages, the throat, and various locations within the lungs, such as the bronchi, bronchioles and alveolar regions. The ability to deliver drugs to a target area depends inter alia on the aerodynamic sizes of the particles or droplets. As currently believed to be understood, particles having an aerodynamic diameter of less than 2 μm are considered to be potentially optimal for deposition in the alveolar region of the lung. Particles that have an aerodynamic diameter of between 2 and approximately 5 μm may be more suitable for delivery to the bronchiole or bronchi regions. Particles with an aerodynamic size range greater than 6 μm, and more preferably 10 μm, are typically suitable for delivery to the laryngeal region, throat or nasal passages.

In most cases, it is desired to achieve a high inhalable fraction and a high delivery efficiency, i.e., the fraction of the initial dose of drug that reaches the desired region, in particular, in the lung. This depends on various factors, in particular, on the characteristics of the generated spray plume, such as propagation velocity of the plume, particle size and its distribution, fraction of small particles, fraction of gas or the like. In the present invention, the desired spray plume characteristics include preferably a small particle size, a high fraction of drug particles with a diameter of 6 μm or less, a low propagation velocity and/or a long duration of spray generation and possible inhalation.

The present invention relates to the dispensing of a preferably medical formulation. The term "formulation" relates, in particular, to a powder, but may include or relate to a liquid as well. Consequently, the fine "particles" may be either solid or liquid. The term "liquid" is to be understood preferably in a broad sense as covering, inter alia, solutions, suspensions, suslutions, mixtures thereof or the like. More particularly, the present invention relates to the dispensing of formulations for inhalation, such as medical formulations containing or comprised of at least one drug.

In the following, the description will focus mainly on powder formulations. However, the same applies for liquid formulations.

In particular, the present invention is concerned with dry powder inhalers for the delivery of drugs to the lungs. Many dry powder inhalers are on the market or have been proposed. There are two main types, namely the passive ones and the active ones. In passive inhalers, all the energy required for de-agglomerating the powder and transferring the powder to the lungs is provided by the breathing of a user, respectively the patient. In active inhalers, there is an additional source of energy to help to de-agglomerate the powder.

Most powder inhalers are of the passive type where the powder is inhaled by the patient without the aid of an additional energy source. The problem with passive inhalers is that the inhalable fraction, or the proportion of powder that actually enters the lungs, is largely dependent on the breathing of the patient. The de-agglomeration of the powder and hence the inhalable fraction is a function of the flow rate of inhaled air through the device and, therefore, varies greatly from patient to patient.

Dry powder inhalers are subdivided into single dose and multi-dose devices or inhalers. Multi-dose inhalers are further subdivided into pre-metered types where the doses are stored individually and into metering inhalers where each powder dose is metered in the device.

Multi-dose pre-metered inhalers have the advantage that the single doses are metered under strict factory conditions and the powder can quite easily be isolated from the atmosphere. In many applications, the active drug powder is mixed with a carrier, such as lactose, which tends to absorb humidity from the atmosphere which makes it stick together and difficult to de-agglomerate.

The present invention relates in particular to an active, gas (preferably air) powered, pre-metered multi-dose dispensing device for dispensing a formulation containing or comprised of a drug, such as a dry powder inhaler.

U.S. Pat. No. 4,627,432 discloses a device for administering medicaments to patients, namely an inhaler. The inhaler comprises a disk-like blister pack having a plurality of blister pockets arranged in a circle. Each blister pocket contains a dose of the powder. A plunger can open a blister pocket. When a blister is opened, the medicament can be withdrawn by a patient inhaling through a mouthpiece.

It is difficult to empty the respective blister pocket completely during a dispensing operation. Incomplete emptying results in decreased delivery efficiency. Some powder may be lost in the inhaler and not dispensed because the known solutions require relatively long paths for the powder until the powder reaches a nozzle and is actually dispensed. This might reduce the delivery efficiency further in addition, de-agglomeration of the powder is difficult and the powder may block an outlet nozzle that is used for dispensing multiple doses one after the other.

SUMMARY OF THE INVENTION

A primary object of the present invention is to provide an improved dispensing device, storage device and method for dispensing a preferably medical formulation, in particular, wherein a high delivery efficiency, a good sealing and/or the desired spray plume characteristics can be achieved.

The above object is achieved by a dispensing device, storage device and method according to the invention as described herein.

One aspect of the present invention is to provide a carrier with multiple inserts, wherein each insert contains one dose of the formulation that is to be dispensed. Thus, it is possible to seal the carrier in an optimized manner, i.e., very effectively. Further, the inserts may store the formulation in an optimized manner so that easy, effective and complete delivery of the respective dose of the formulation can be achieved.

According to a preferred embodiment, the inserts may be respectively used to open an associated sealing, in particular, by pushing the respective insert through the associated sealing of the carrier or at lest partially out of a cavity of the carrier containing the respective insert.

According to another embodiment, each insert comprises at least one duct or nozzle for dispensing the respective dose of the formulation and generating the desired spray with fine particles.

Further aspects, advantages and features of the present invention will be apparent from the following detailed description of preferred embodiments with reference to the accompanying drawings.

DETAILED DESCRIPTION OF THE INVENTION

In the figures, the same reference signs are used for same or similar components, wherein same or similar characteristics, features or advantages are or can be realized or achieved, even if a repeated discussion is omitted. Further, the features and aspects of the different embodiments can be combined in any desired manner and/or used for other dispensing devices or methods for dispensing, in particular, medical formulations for inhalation.

Figure 1:
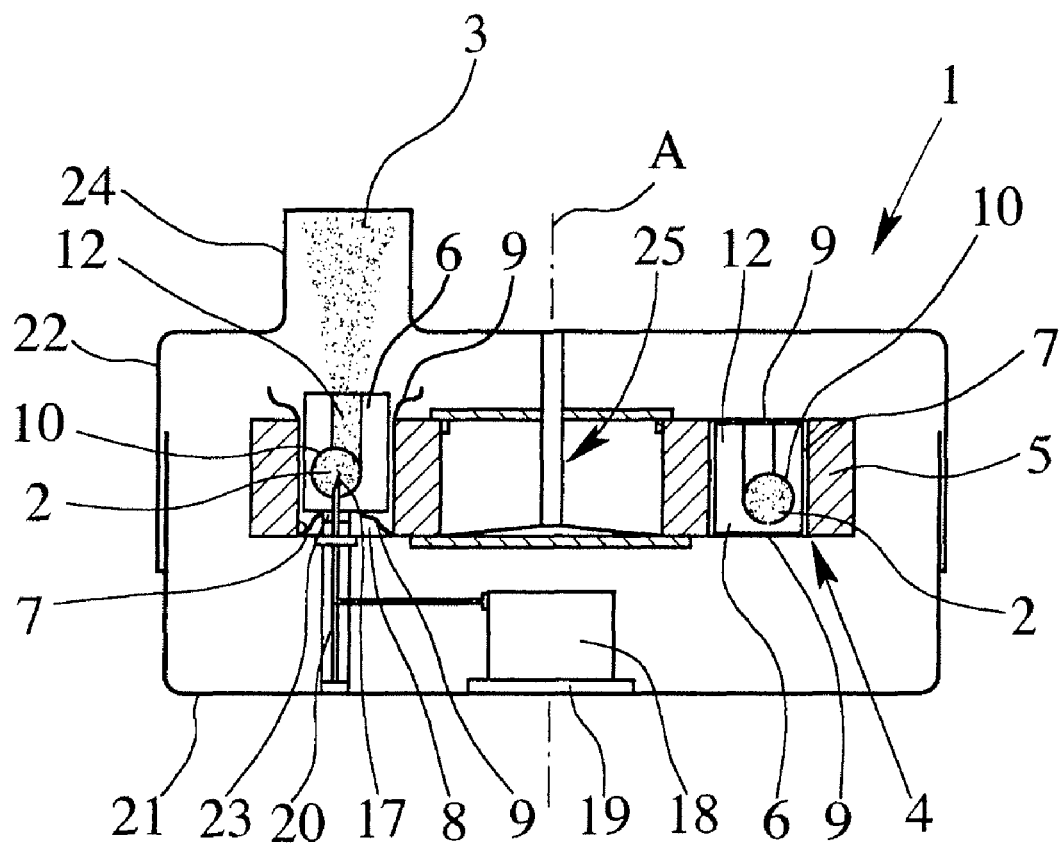
FIG. 1 is a schematic sectional view of a dispensing device with a storage device according to one embodiment of the present invention during dispensing.

FIG. 1 shows in a schematic sectional view—for illustration purposes not in scale—a dispensing device 1 according to the present invention. The dispensing device 1 is an active device, in particular gas powered. Preferably, the dispensing device 1 is a preferably oral or nasal inhaler, in particular a dry powder inhaler, for a user, respectively the patient (not shown).

The dispensing device 1 may be used for dispensing any formulation 2 as defined in the introductory part of the description. In particular, a medical formulation 2 or a formulation 2 for inhalation will be used. The formulation 2 preferably contains or consists of at least one drug. When the formulation 2 is dispensed, a spray 3 is generated as indicated in FIG. 1. The spray 3 includes fine particles (solid and/or liquid) and preferably has the desired spray plume characteristics.

The formulation 2 may be a liquid, in particular a solution, a suspension or any mixture thereof, i.e. a so-called suslution. Preferably, when different drugs are dispensed simultaneously, a suslution may be used. The principle of the suslution is based on that different drugs may be combined in one formulation simultaneously as a solution and as a suspension. In this respect, reference is made to EP 1 087 750 A1 and corresponding U.S. Pat. No. 6,423,298 which is incorporated by reference.

Preferably, the formulation is a powder. The powder may be a pure drug or a mixture of at least two drugs. In addition, the powder may contain at least one other material, in particular a drug carrier such as lactose. In the following, the description focuses on powder as formulation 2. However, this applies in a similar manner if a liquid formulation 2 is used.

Preferably, the mean diameter of the powder particles is about 2 to 7 μm, in particular, 6 μm or less. This applies, in particular, if the powder does not contain any drug carrier, such as lactose.

If the powder contains a drug carrier, such as lactose, and at least one drug, the powder 2 may have a particle size of 20 to 300 μm, in particular, about 30 to 60 μm. However, the de-agglomeration, which will be described later in more detail, may result even in this case in a spray 3 with a smaller particle size, e.g., of about 10 μm or less. In particular, the drug may be separated from the drug carrier during de-agglomeration so that primarily the drug will be inhaled due to its small particle size of about 2 to 6 μm and the larger drug carrier will be swallowed when using the dispensing device as an inhaler. Alternatively or additionally, breaking or opening of the drug carrier is possible during de-agglomeration.

The diameters mentioned above and below may be understood as mass medium aerodynamic diameters and/or may apply to the particle size or a fraction of the particles of the spray 3.

The dispensing device 1 is adapted to receive or comprises a storage device 4 for storing preferably multiple and pre-metered doses of the formulation 2. The storage device 4 may be integrated into the dispensing device 1 or form part of the dispensing device 1. Alternatively, the storage device 4 may be a separate part that can be inserted or connected with the dispensing device 1 and optionally replaced.

The storage device 4 comprises a carrier 5 with at least one insert 6, preferably multiple inserts 6. In particular, the carrier 5 may comprises 20 to 100, preferably 30 to 60 inserts 6. Each insert 6 contains preferably one pre-metered dose of the formulation 2. However, each insert 6 may also contain more than the formulation 2, i.e., different formulation 2. Additionally or alternatively, different inserts 6 may contain different formulations. In the present invention, "different" means, in particular, that the formulations 2 differ in at least one of the composition, the drug, the dose or amount, the concentration, and consistency of the formulation 2, e. g., liquid or dry or powder 5.

The carrier 5 comprises multiple cavities 7 for receiving the inserts 6. In particular, each insert 6 is located in a separate cavity 7.

The cavities 7 are separate from each other and, in particular, sealed relative to each other.

In the present embodiment, each cavity 7 comprises two preferably opposed openings 8. Before use, the openings 8 are covered by respective sealings 9 which are preferably formed by foils on opposite sides of the carrier 5, in particular, metallic foils, plastic foils, multi-layer arrangements or the like.

Figure 2:
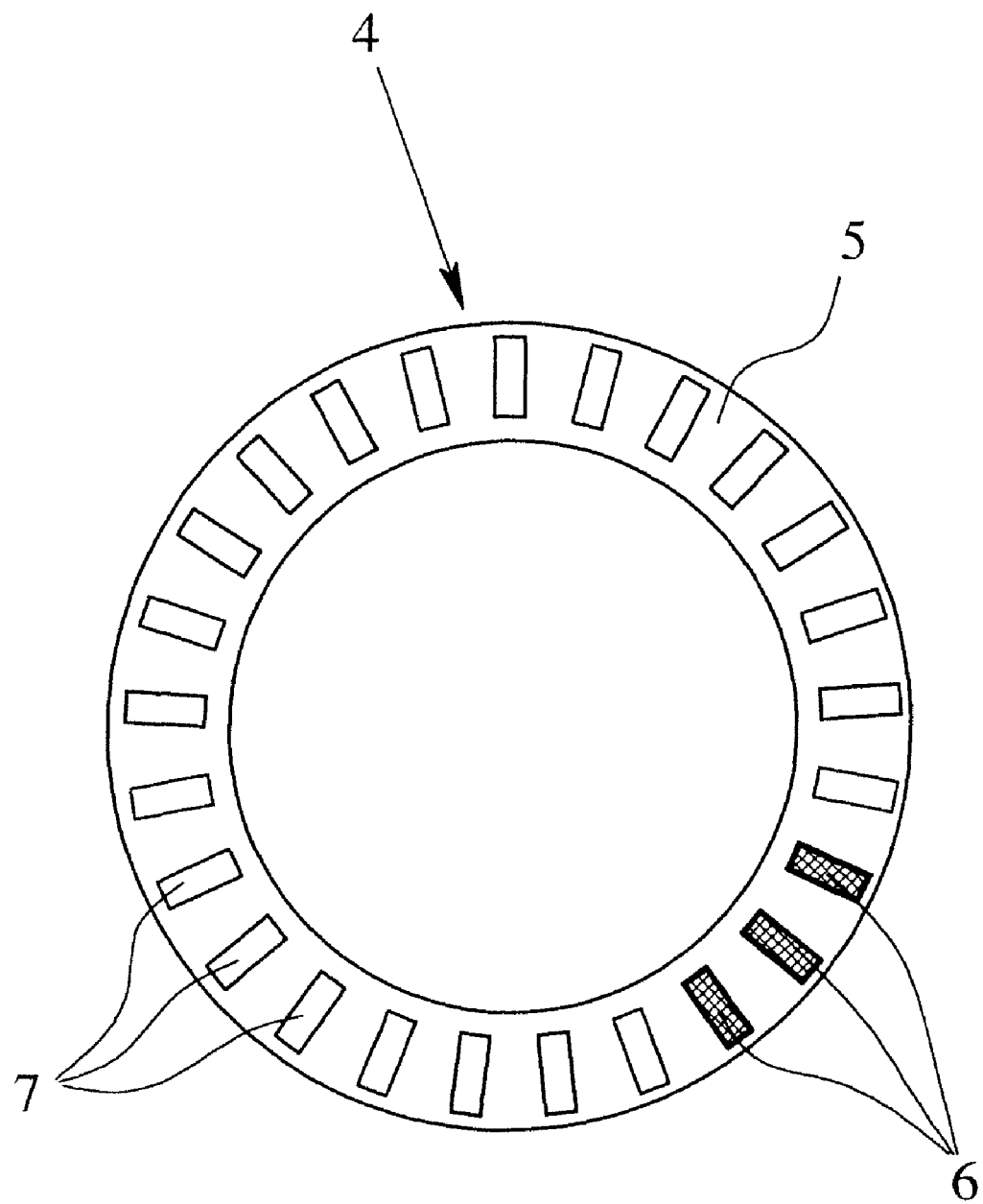
FIG. 2 is a top view of the storage device with multiple inserts.

FIG. 2 shows the storage device 4 with the carrier 5, wherein the top sealing 9 and some inserts 6 are omitted. In this embodiment, the carrier 5 is ring-shaped and the cavities 7 extend at least substantially in an axial direction. The cavities 7 are distributed around or along the perimeter of the carrier 5, preferably in an equally spaced manner.

The carrier 5 may be a molded element, a ring, a strip, a cartridge, a blister or a container. Preferably, the carrier 5 is rigid or at least essentially stiff.

Preferably, the carrier 5 is made of foil, plastics, ceramics and/or composite material, in particular of thermoplastics or thermoplastic elastomers and for sealings of elastomers or silicone.

Each cavity 7 preferably forms a guide for the associated insert 6, in particular, so that the insert 6 can be moved in at least one direction at least partially out of the cavity 7.

FIG. 1 shows a situation, wherein the insert 6, on the left side, has already been pushed at least partially out of its associated cavity 7 and/or through a respective sealing 9 of its associated cavity 7 for opening the sealing 9. The insert 6 shown on the right side of FIG. 1 is still within its closed and sealed cavity 7.

Each insert 6 is preferably produced separately from the carrier 5 and, then, inserted into its respective cavity 7.

Preferably, each insert 6 is made of foil, plastics, ceramics and/or composite material, in particular, of thermoplastics or thermoplastic elastomers and for sealings of elastomers or silicone.

According to a preferred embodiment, the carrier 5 and/or the inserts 6 are made of at least one of the following materials or any mixture or blend thereof:

ABS (acrylonitril-butadiene-styrene copolymer); SAN (styrene-acrylonitril-copolymer); PBT (polybutylene terephthalate); PC (polycarbonate); CA (cellulosic acetate); EVA (ethylene vinylacetate copolymer); PA (polyamide); PE (polyethylene); PP (polypropylene); PMMA (polymethylmethacrylate); POM (polyoxymethylene, polyacetal); PPS (polyphenylene sulfide); PS (polystyrene); PBTP (polybutylene terephthalate); TPU (thermoplastic polyurethane); blend of PC and PBTP; blend of PC and ABS; LCP (liquid crystal polymers); PHCS (polypyrrol or polythiophene); PPA (polyphthalamide); PSU (polysulfone); PTFE (polytetrafluorethylene); PUR (polyurethane); SB (styrene-butadiene copolymer); PIB (polyisobutylene); PAN (peroxyacylnitrate); PET (polyethylene terephthalate); AMMA (acrylonitril-methymethacrylat copolymer); PAR (polyarylate); PEEK (polyetheretherketone).

Each insert 6 may form a preferably block-like unit and be rigid. Alternatively, the inserts 6 may be flexible. In particular, each insert 6 may be a unitary unit or may be formed of multiple elements. Each insert 6 may be a molded element, a cartridge, a blister, a capsule, a container or the like.

In the following, a preferred construction of one insert 6 is explained. Preferably, all inserts 6 are identical. However, it is also possible that all or some of the inserts 6 are different. For example, two or more groups of different inserts 6 can be provided. It is possible that one group has a different dose or different formulation 2 than the other group. For example, the inserts 6 of the different groups could be arranged alternately one after the other so that a patient or user may use, for example, each morning an insert 6 of one group and each evening an insert 6 of the other group.

Figure 3:
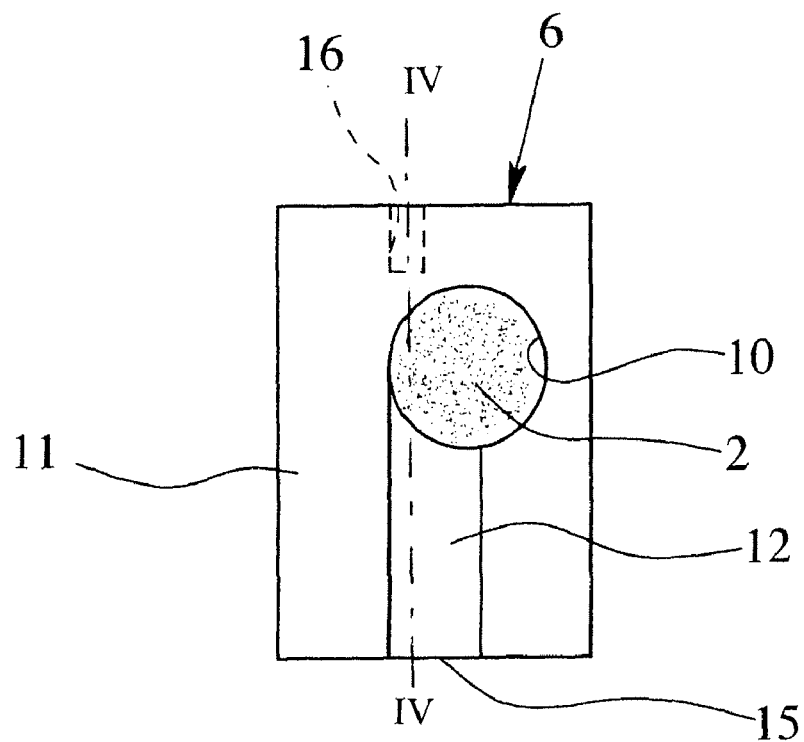
FIG. 3 is a schematic sectional view of an insert.

Each insert 6 comprises a storage cavity 10 for a single dose of the formulation 2. The schematic sectional view according to FIG. 3 and schematic sectional view according to FIG. 4 along line IV-IV of FIG. 3 show a preferred embodiment of the insert 6. The insert 6 comprises a storage chamber 10 for the formulation 2. In the present embodiment, the storage chamber 10 is preferably formed in a molded base member 11 of the insert 6.

The insert 6/base member 11 further comprises a duct 12 or the like for discharging the formulation 2 during the dispensing operation. The formulation 2 is dispensed through the duct 12 during the dispensing operation, in particular, for de-agglomerating the powder and/or forming the spray 3.

Figure 5:
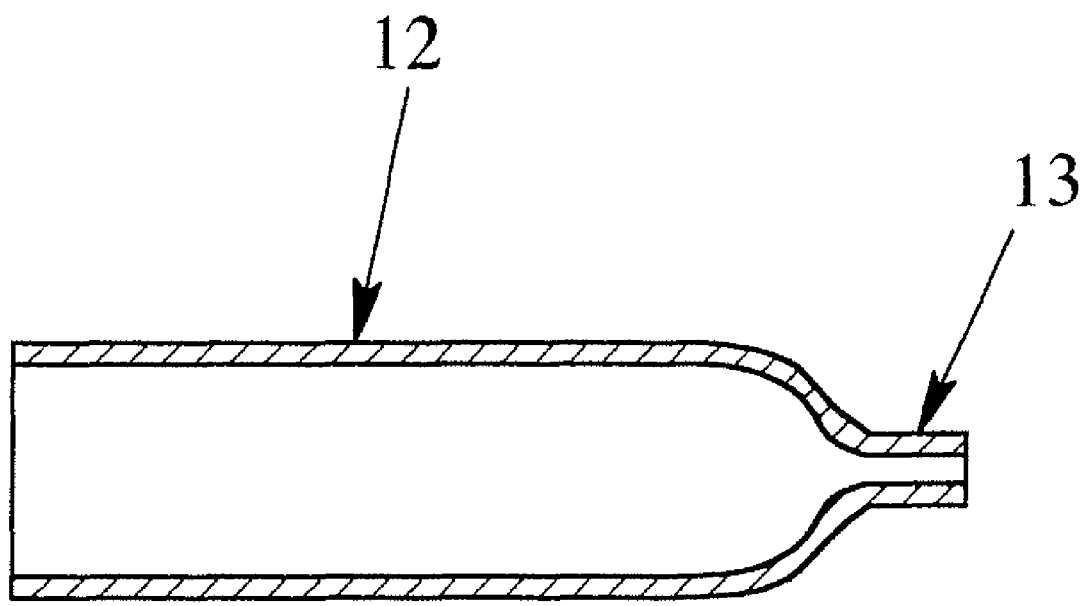
FIG. 5 is a schematic longitudinal sectional view of a duct with a nozzle.

The duct 12 can comprise a nozzle (restriction) 13 preferably at the outlet, as shown in the schematic longitudinal sectional view according to FIG. 5. Alternatively, the nozzle 13 or any other suitable nozzle arrangement could be used instead of or in any other combination with duct 12.

Figure 4:
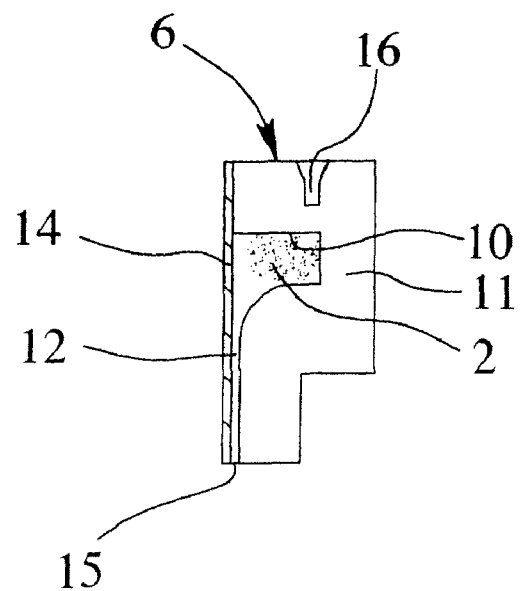
FIG. 4 is another schematic sectional view of the insert.

Preferably, the duct 12/nozzle 13 is formed by the base member 11, in particular, by a recess, groove or the like in the base member 11 and by an associated cover member 14 as shown in FIG. 4. In particular, the duct 12 forms a channel from the storage chamber 10 to an outlet 15 of the insert 6 for discharging the formulation 2 as spray 3 as shown in FIG. 1.

Figure 6:
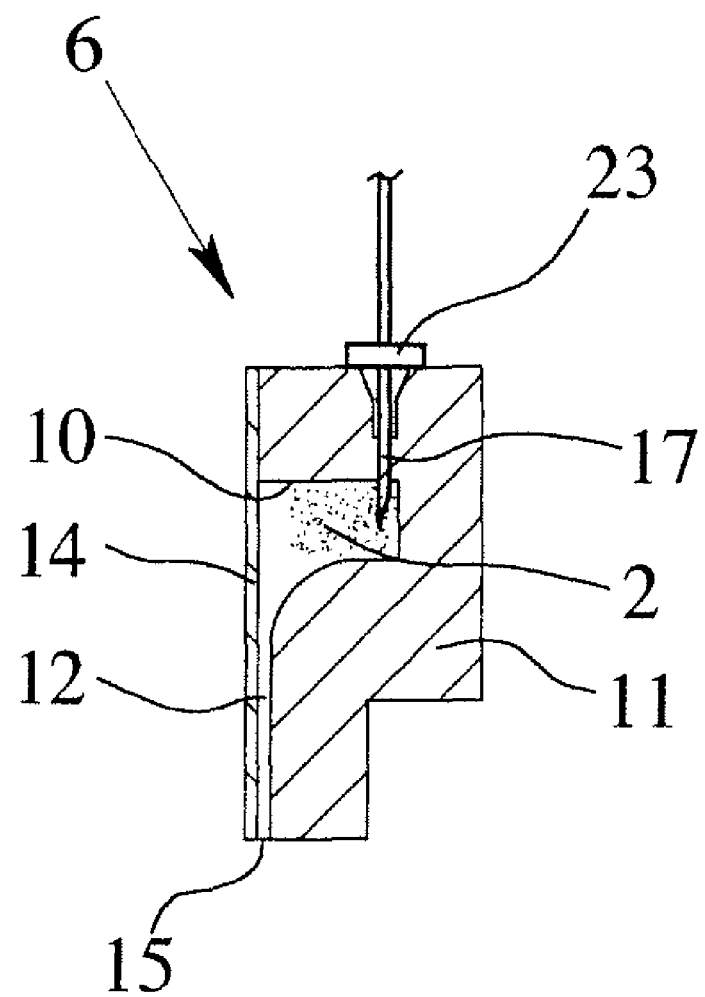
FIG. 6 is a schematic sectional view similar to FIG. 4 with an inserted piercing element.

The insert 6 comprises preferably an inlet for supplying pressurized gas into the storage chamber 10 to force the formulation 2 through the duct 12/nozzle 13 and to dispense the formulation 2 as spray 3. In the present embodiment, the inlet is preferably designed as a tube-like recess or blind bore 16 formed in the base member 11. Preferably, the recess 16 is not directly connected to the storage chamber 10, but separated by an intermediate wall. This wall can be penetrated, e.g., by a piercing element 17, such as a needle, as shown schematically in FIG. 6, or by any other suitable opening and/or supply means, in particular, when the respective insert 6 is connected to a gas supply as explained in the following. In the present invention, the expression "piercing element 17" preferably covers also all other suitable types of means for opening the carrier 5, a cavity 7 and/or an insert 6 and/or for directly or indirectly supplying gas to an insert 6 or its respective storage chamber 10.

The dispensing device 1 uses pressurized gas to force the formulation 2 through the duct 12/nozzle 13 to de-agglomerate the powder and/or to generate the spray 3 with fine particles. Preferably, the dispensing device 1 comprises a means for providing pressurized gas, in the present embodiment an air pump 18 which can preferably be actuated or operated manually as indicated by handle or actuator 19. In particular, the air pump 18 comprises or is formed by a bellows. However, it could be also a piston-cylinder-arrangement. Instead of the air pump 18, the means for providing pressurized gas can be, e.g., a capsule, container or the like containing pressurized or liquefied gas for powering the dispensing device 1, i.e., dispensing the formulation 2 as desired.

The air pump 18 may provide a gas pressure of less than 300 kPa, in particular, about 50 to 200 kPa. This is preferably sufficient for operating the dispensing device 1. If liquefied gas or a container with pressurized gas is used, the gas pressures might range from 100 kPa to about 700 kPa. Then, the pressure may be reduced or throttled to the preferred pressure range before supplying the gas to the storage device 4, in particular, the storage chamber 10 of the respective insert 6.

Preferably, all pressure values mentioned in the present description are gauge pressures, i.e., pressure differences. All pressure values relate to the pressure in a gas storage, such as a container with pressurized or liquefied gas or provided by air pump 18 or relate to the pressures acting in the chamber 10 and/or in the duct 12.

FIG. 1 shows that the dispensing device 1 comprises a mechanism 20 for connecting the inserts 6 individually to the gas supply, in particular, to the air pump 18. The mechanism 20 comprises preferably the piercing element 17 or any other suitable connecting element. In the present embodiment, the mechanism 20 is associated with a first (lower) housing member 21 of the dispensing device 1. The dispensing device 1 also comprises a second (upper) housing member 22 which may support the storage device 4/carrier 5.

According to one embodiment, the first and second housing members 21, 22 can be moved relatively to each other, in particular, in an axial direction with respect to the rotational axis of the carrier 5 or parallel to the orientation of the cavities 7 (FIG. 1 shows housing member 21 telescoped into housing member 22). This relative movement enables the mechanism 20, in particular, its piercing element 17, to connect or penetrate the respective insert 6 adjacent to the mechanism 20.

In particular, the relative movement results in a first phase in that the piercing element 17 penetrates the sealing 9 and, then, is inserted into the recess 16 and through the end wall into the storage chamber 10 and, thus, connects the respective insert 6 to the gas supply. In the next phase, i.e., during the further movement, a shoulder or abutment 23 (better shown schematically in FIG. 6) abuts at the insert 6 so that the insert 6 is pushed through the other opening 8 and through the respective sealing 9 at least partially out of its cavity 7. This final situation is shown in FIG. 1.

The relative movement of the first and second housing members 21, 22 can also actuate the air pump 18 or open any other gas storage. In the present embodiment, the air pump 18 may be actuated separately by means of the actuator 19.

For dispensing, the gas is supplied under pressure to the storage chamber 10 via the piercing element 17 or any other suitable supply element.

The gas (air) generates a respective flow in the storage chamber 10 to force the complete dose through the duct 12.

The powder will be discharged, in particular, forced, through the duct 12, with a comparatively low gas pressure (preferably less than 300 kPa, in particular, about 50 to 200 kPa). This low gas pressure, which is significantly lower than the gas pressures in the prior dispensing devices, enables a respectively low discharge velocity, and therefore, a spray 3 with a slow propagation velocity.

Preferably, the storage chamber 10 forms a mixing chamber for mixing the gas with the powder. The chamber 10 is preferably designed such that the gas can generate swirls or eddies for better mixing the powder with the gas. Preferably, the chamber 10 is substantially circular in cross section, in particular cylindrical. However, other shapes are also possible.

Further, the chamber 10 is formed with no sharp edges, corners or the like, but has a smooth contour so that the gas can sweep all chamber surfaces to prevent powder accumulating on said surfaces and to ensure or allow complete discharge of the powder. In particular, the gas inlet formed by the piercing element 17 or any other supply element is located opposite to the outlet, i.e., duct 12 and/or nozzle 13, with regard to the axial or outlet direction.

The storage device 4 may comprise only one insert 6 with one storage chamber 10 for a single dose or with multiple storage chambers 10 with different formulations 2; in this case, the storage device 4 is for a single dose or use only, but comprises preferably multiple inserts 6, and thus, contains multiple doses of the formulation 2, which can be dispensed subsequently.

During the dispensing operation, the spray 3 is preferably directly generated by the respective insert 6 or its duct 12/nozzle 13 and output into a mouthpiece 24 of the dispensing device 1, as shown in FIG. 1, for inhalation by a patient or user (not shown).

After dispensing one dose or for dispensing the next dose, the piercing element 17 will be withdrawn from the connected insert 6, in particular due to an opposite relative movement of the first and second housing members 21, 22. During this opposite movement or by a separate actuation or during the movement for connecting the next insert 6 to the gas supply, the carrier 5 will be indexed one step further or to the next insert 6, in particular, rotated my means of an indexing or transport mechanism (not shown). This mechanism is preferably operated by the relative movement of the first and second housing members 21, 22 or by actuating another actuator, by opening a cap of the dispensing device 1 or the like.

In the present embodiment, the carrier 5 is preferably rotatable around axis "A" shown in FIG. 1 and supported by a respective holder 25, preferably connected to the second housing member 21. In particular, the dispensing device 1 can be opened and the storage device 4/carrier 5 can be inserted or replaced.

It is noted that the first and second housing members 21, 22 may be pivoted relatively to each other alternatively or additionally to the relative axial movement described above. Then, the mechanism 20 may be adapted respectively in order to provide the desired function, in particular, the axial connection and displacement of the respective insert 6.

It is also noted that the inserts 6 are preferably open, i.e., not sealed. Instead, experiments have shown that sealing of the carrier 5/the cavity 7 is sufficient. The duct 12/nozzle 13 is preferably so small that the formulation 2 is not discharged, even with opened sealing 9 and during strong shaking of the dispensing device 1/storage device 4.

Further, the inserts 6 and cavities 7 are preferably adapted to each other such that the sealings 9 contact the end faces of the inserts 6 and, thus, cover the outlets 15. This may further prevent that any formulation 2 dissipates through the duct 12/outlet 15 before the desired dispensing.

Furthermore, the cross sections of the inserts 6 and the cavities 7 are preferably polygonal, in particular rectangular, in order to avoid that the inserts 6 may pivot within the cavities 7. However, if the inserts 6 are rotatably symmetrical with respect to the recess 16 or any other connection/inlet for gas supply and with respect to its outlet 15, the inserts 6 may also be cylindrically and/or can rotate within the cavities 7. This may facilitate insertion of the inserts 6 into the cavities 7 during production.

Figure 7A:
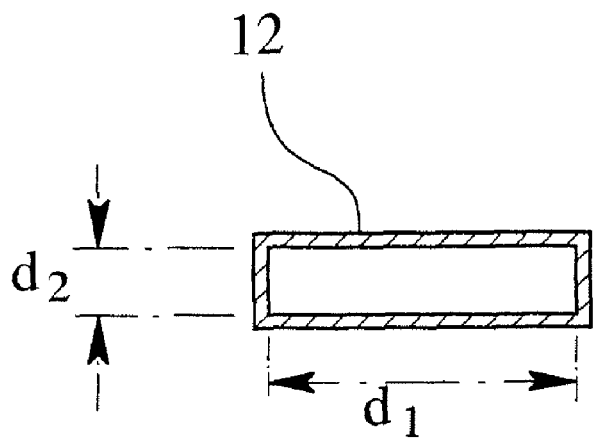
FIG. 7a-7c is cross sectional views of ducts of the insert with different cross sections.
Figure 7B:
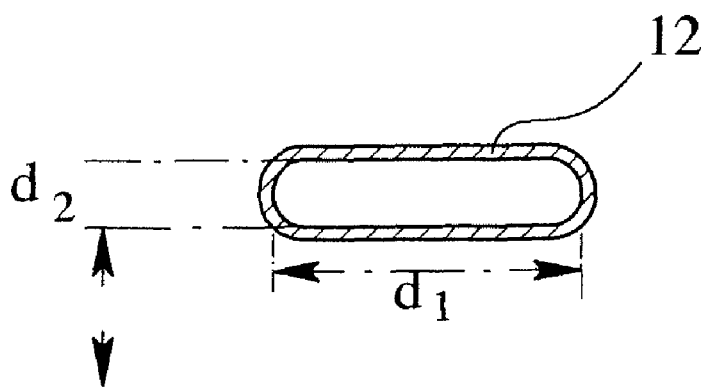
Figure 7C:
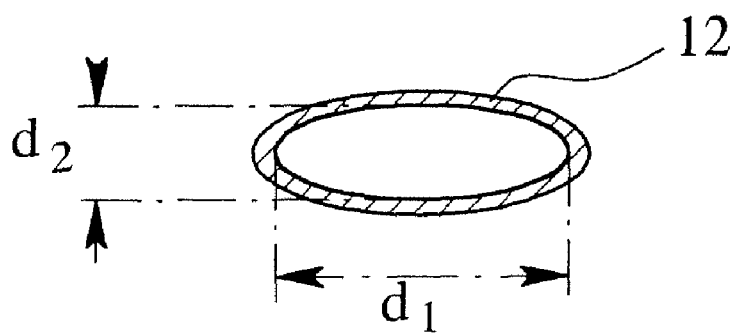

According to a preferred aspect, the duct 12 has a flat (inner) cross section. FIG. 7a to 7c show potential cross sections of the duct 12. FIG. 7a shows a substantially rectangular cross section. FIG. 7b shows a flat cross section with two opposite straight sides connected by two curved portions. FIG. 7c shows an oval or elliptical cross section.

A cross section is considered to be flat when the ratio of the largest side d1 to the smallest side d2 of the cross section is at least 2.0. Preferably, the ratio is between 3 to 50, and in particular, about 5 to 70. It is pointed out that the cross sections shown in FIG. 7 are not to scale.

The largest side d1 is preferably between 0.5 to 5 mm, in particular, 1 to 3 mm. Most preferably, the ratio of the largest side d1 to the (desired) fine particle size (mass mean diameter of the powder particles or drug particles of the spray 3) is less than 500, preferably less than 300, in particular about 30 to 300.

The smallest side d2 is preferably between 0.05 to 0.5 mm, in particular, about 0.07 to 0.25 mm. Most preferably, the ratio of the smallest side d2 to the mass mean (desired) fine particle size (mass mean diameter of the powder particles/drug particles of the spray 3) is less than 50, preferably less than 30, in particular about 3 to 20.

The length of the duct 12 means the length with the flat cross section. Thus, the duct 12 can have a larger length, i.e., further portions with another cross sectional shape and/or with a larger cross sectional area so that the influence of these other portions is low on the mixture of gas and powder in comparison to the portion of the duct 12 with the flat cross section. However, the cross section area and/or the shape of the flat cross section may vary over the length of the duct 12 (the portion with the flat cross section). Thus, it is possible that the cross sectional area of the duct 12 tapers from the inlet to the outlet or vice versa.

Most preferably, the duct 12 comprises at least one portion of flat cross section with constant cross section area, i.e. constant diameter and/or shape.

The length of the duct 12—i.e., the portion with flat cross section—may be in the range of 3 mm to 80 mm, in particular, 5 to 15 mm. Preferably, the duct length is adapted to the mean hydraulic diameter of the duct 12 such that the ratio of the length of the duct 12 to the mean hydraulic diameter is at least 5, in particular about 10, preferably 20 to 60, or more, wherein the hydraulic diameter is defined as the ratio of four cross sectional areas over the duct perimeter.

The diameter of the preferably circular or cylindrical or conical chambers 10 depend on the volume or mass of the respective dose of the formulation 2. A single dose may have e.g., 1 to 2 mg (pure drug without carrier) or 2 to 10 mg (blend of drug with carrier, in particular lactose). In the first case, the range of the diameter is preferably 1.5 to 2.5 mm. In the second case, the range of the diameter is preferably between 2 and 5 mm. Preferably, the cross section of the duct 12 varies in a similar manner. For example, the smallest side d2 is about 0.07 to 0.1 mm in the first case and about 0.15 to 0.25 mm in the second case. The larger (inner) side d1 does not depend so strongly on the powder or spray particle size. Preferably, it is in the range of about 1 to 2 mm in the first case and 1 to 3 mm in the second case.

The mean hydraulic diameter of the duct 12 is preferably less than 1 mm, in particular, 0.1 mm to 0.6 mm.

Preferably, the duct 12 is molded and/or formed by a flat groove with a cover.

According to another embodiment, the dispensing device 1 may comprise a common duct 12/nozzle 13 for dispensing the dose of the formulation 2 from one insert 6 after the other. In this case, the insert 6 may be pressed with its outlet 15 against this common duct 12/nozzle 13 (not shown) which may be arranged e.g., above the elevated insert 6 shown in FIG. 1, i.e., within or below the mouthpiece 24.

Each insert may comprise multiple ducts 12 for dispensing simultaneously one dose, in particular for increasing the total mass flow or output so that a desired dose can be discharged or dispensed in a sufficiently short time as desired and/or required.

Figure 8:
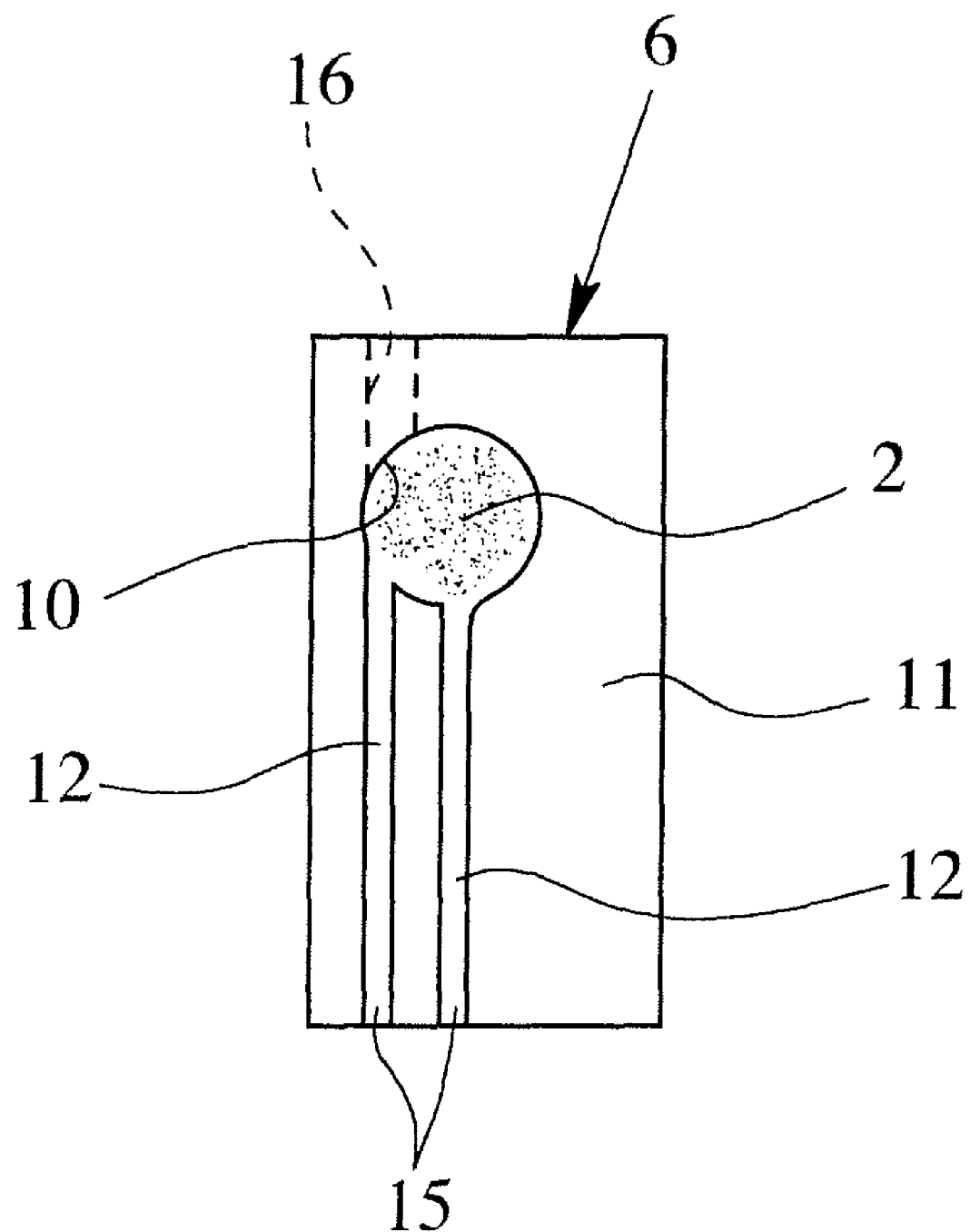
FIG. 8 is a schematic sectional view of another insert.

FIG. 8 shows another embodiment of the insert 6 in a sectional view similar to FIG. 3. Here, the insert 6 comprises two ducts 12 associated or connected to the same storage chamber 10.

Figure 9:
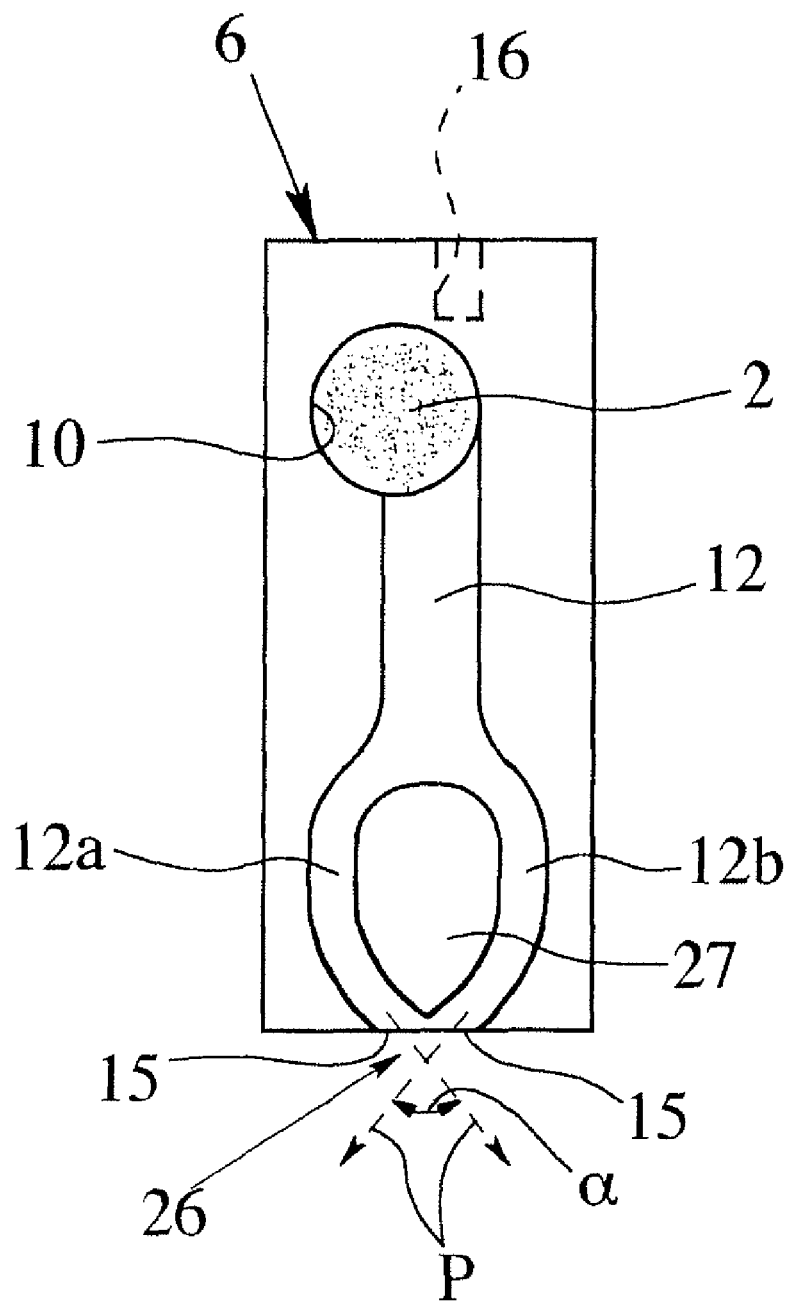
FIG. 9 is a schematic sectional view of a further insert.

FIG. 9 shows, in a schematic sectional view, another insert 6 with a means for slowing down the velocity which forms a multiple jet impinging means 18. The means 18 forms multiple—at least two—jets P which impinge, i.e., hit each other as indicated in FIG. 9. In this embodiment, the duct 12 divides into two sections 12a, 12b that are designed such that the openings or outlets 15 are inclined to each other so that the jets P ejecting from the portions 12a, 12b are inclined to each other and impinge. For example, a flow divider 27 or any guiding means can be located in the flow path to form the at least two sections 12a, 12b of the duct 12 as shown in FIG. 9.

It has to be added that the cross sections of the duct sections 12a, 12b are preferably not flat, but can have any suitable cross sectional shape.

The impinging angle α between the jets P is between 30° to 180°, preferably at least 90° for powder, in particular, about 90° to 150°. The impinging of the jets P results in a decrease of the velocity of the spray 3 and/or in a de-agglomeration of the powder or forming of small droplets and/or in separation of drug particles from a carrier and/or in better focusing of the spray 3. These effects depend on the impinging angle α. A larger impinging angle α tends to result in better effects. In contrast to liquid jets, an impinging angle α of 90° and more is possible and preferred for powder. These angles also apply for the following embodiments.

The duct 12 is preferably at least tangentially connected to the storage chamber 10 in the embodiment shown in FIG. 9. Preferably, the duct 12 is connected at one axial end of the preferably cylindrical chamber 10, and the gas inlet is connected to the other axial end of the chamber 10. In particular, the gas inlet is connected also tangentially to the storage chamber 10, such that swirls are generated when entering the gas with a swirl direction supporting discharge of the mixture of gas and formulation 2 through the duct 12 which connects tangentially to the rotational direction of the swirl.

It is noted that the present invention, in particular, the dispensing device 1 and/or the storage device 4, can be used for dispensing one drug, a blend of drugs or at least two or three separate drugs. In the latter case, the separate drugs are stored in separate storage chambers 10, and during the dispensing operation, the drugs are mixed either in a common mixing chamber or in their respective storage chambers 10 with the gas. Further, the separate drugs can be discharged through a common duct 12 nozzle 13 or through separate ducts 12 nozzles 13. In the latter case, the separate drugs will be mixed after leaving the separate ducts 12/nozzles 13 or in the mouthpiece 24 or in any other suitable (additional) mixing chamber. It is also possible to mix the separate drugs by impinging jets of the separate drugs. For dispensing the separate drugs, it is preferred to use a common gas supply or means for pressurizing gas such as an air pump 18.

Figure 10:
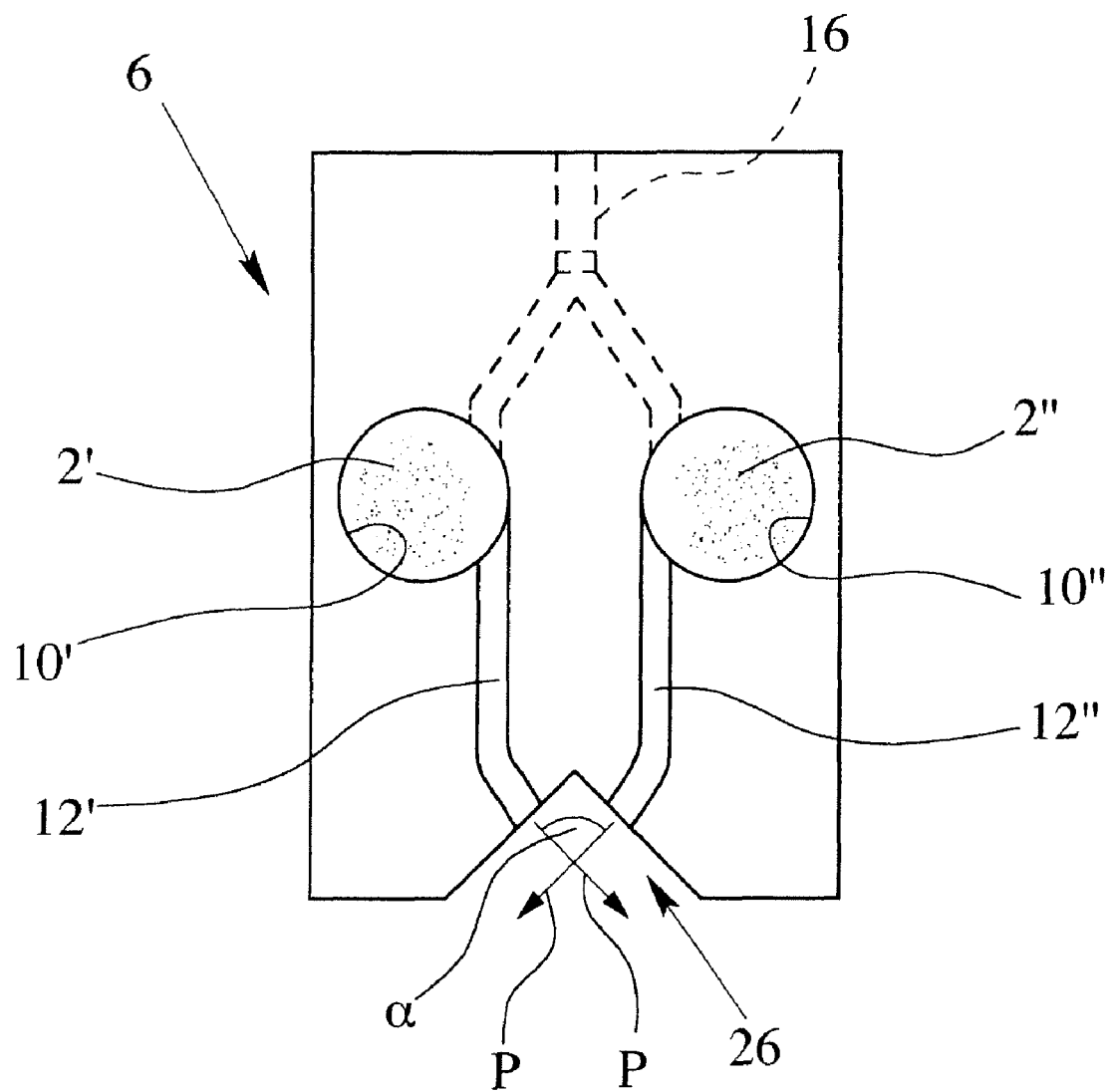
FIG. 10 is a schematic sectional view of a still further insert.

FIG. 10 shows a schematic sectional view of another embodiment of the insert 6. Two different formulations 2', 2" are contained in separate storage chambers 10', 10", respectively. Gas can be supplied via a common inlet/recess 16 to the chambers 10', 10", respectively. The formulations 2', 2" can be dispensed and de-agglomerated by means of separate ducts 12', 12" or separate nozzles (not shown) or the like. The jets P of the separate and different formulations 2', 2" ejecting from the separate ducts 12', 12" are preferably impinged for mixing the separate formulations 2', 2" just when forming the spray 3. The jet impinging means 26 mixes the separate formulations 2', 2", but can also serve to slow down the propagation velocity of the spray 3 and/or to support de-agglomeration of powder formulations 2', 2" or of separating the respective drugs from carriers.

The embodiments according to FIG. 9 & 10 are also suitable for impinging more than two jets P. For example, it is possible to have similar arrangements in the cross-sectional planes perpendicular to the drawing plane resulting in four outlet directions and jets P arranged on the surface of a conus. However, multiple other arrangements with similar effects are possible.

According to another embodiment (not shown), the duct 12 can also be used as a reservoir (storage chamber 10) for the formulation 2. In this case, the separate storage chamber 10 is not required. Then, the duct 12 is designed to enable sufficient mixing of the gas with the formulation 2 and sufficient de-agglomeration of the powder formulation 2.

Preferably, the spray 3 has a mean velocity (taken 20 cm from the outlet 15 or mouthpiece 24) of less than 2 m/s, in particular, less than 1 m/s. Preferably, the mean duration of the spray 3 is at least 0.2 or 0.3 s, in particular, about 0.5 to 25.

Figure 11:
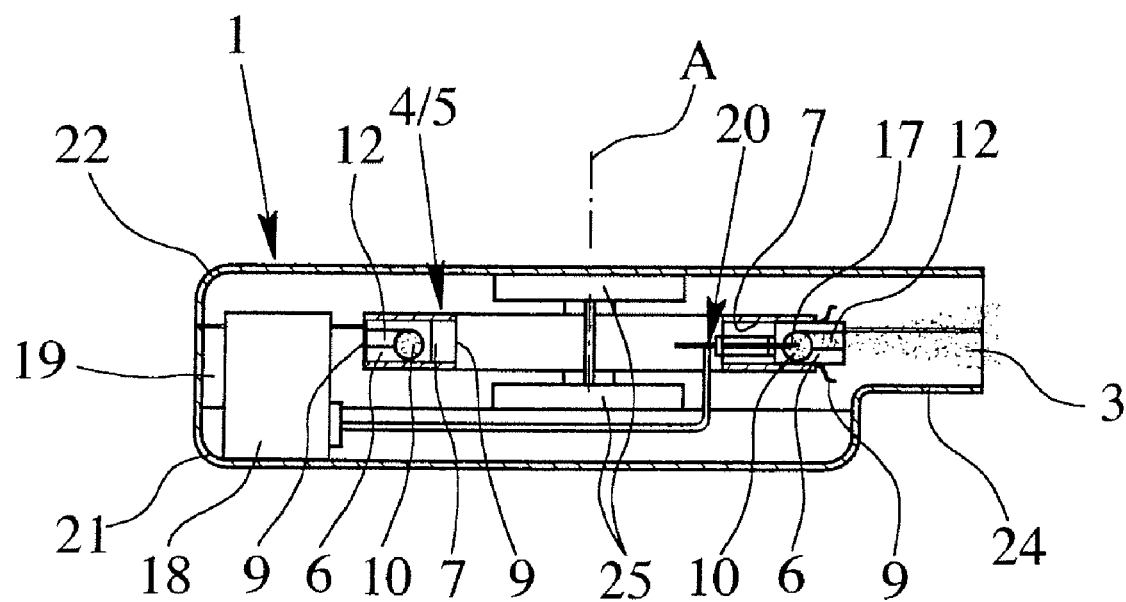
FIG. 11 is a schematic sectional view of a dispensing device with a storage device according to another embodiment during dispensing.

FIG. 11 shows another embodiment of the dispensing device 1. In the following, only differences will be emphasized. The previous explanation, in particular, the description with respect to the embodiment according to FIG. 1, applies in addition or in a similar manner.

In the embodiment according to FIG. 11, the cavities 7 are orientated in tangential or radial direction of the carrier 5. Consequently, the inserts 6 can be individually moved in tangential or radial direction, in particular, outwardly, in order to open the respective outer sealing 9 for dispensing the respective dose of the formulation 2 as indicated in FIG. 11. Accordingly, the mechanism 20 operates in a radial direction for connecting the inserts 6 individually to a gas supply and for pushing the inserts 6 individually at least partially out of the respective cavity 7 and/or through the respective sealing 9. This radial movement allows a very compact design of the dispensing device 1, in particular in axial direction.

Preferably, the mouthpiece 24 and the dispensing direction extents in a radial or tangential direction as shown in FIG. 11.

Preferably, the dispensing device 1 comprises a lever or handle (not shown) for manual actuation in order to index the carrier 5 one step further, i.e., to the next insert 6, and/or to operate the mechanism 20, preferably to connect the respective insert 6 to the gas supply or to move/push the respective insert 6 and open the respective sealing for dispensing the respective dose of the formulation 2.

It is noted that all dispensing devices 1 described above operate preferably only mechanically.

Figure 12:
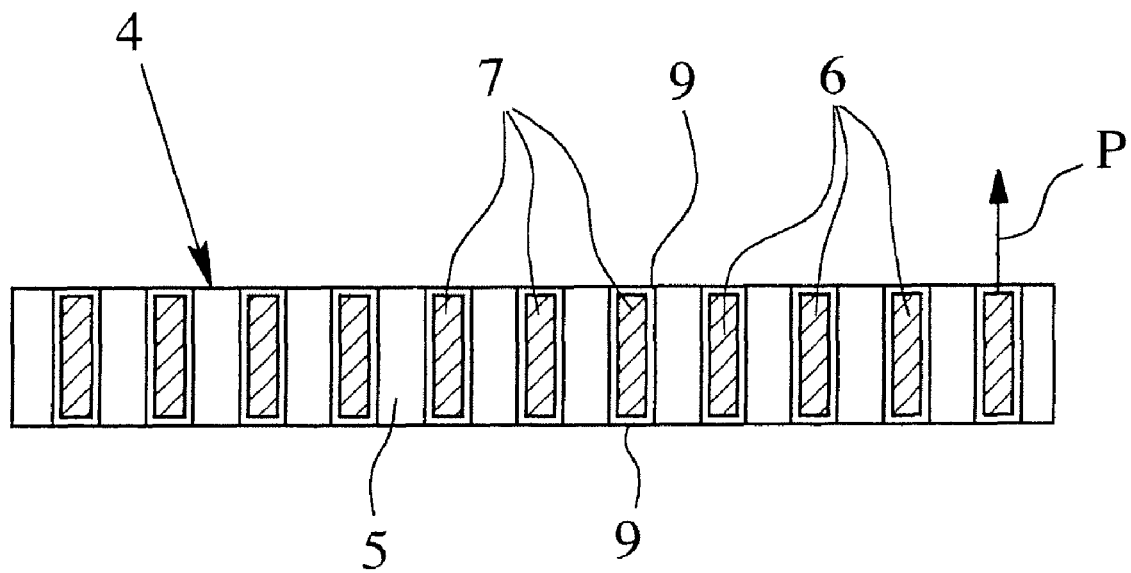
FIG. 12 is a schematic view of another storage device.

FIG. 12 shows another embodiment of the storage device 4/carrier 5. Here, the carrier 5 is like a band or strip, i.e., preferably essentially linear or straight. This facilitates production of the carrier 5 because lamination of the sealings 9 on the opposite straight sides of the carrier 5 is simple. In particular, the sealings 9, such as foil, are laminated to the carrier 5, e.g., by hot sealing or the like.

In the previous embodiments, the carrier 5 is preferably rigid. In the present embodiment, the carrier 5 is preferably flexible and can be bent to a preferably ring-like arrangement and connected—e.g., by gluing—with its ends to a closed belt or a loop.

The inserts 6 are preferably rigid, in particular, if formed by molded elements or the like. However, the inserts 6 may be alternatively flexible, in particular, if formed by blisters or the like.

The arrow P indicates the possible movement of one of the inserts 6 for opening the respective sealing 9.

According to another embodiment (not shown), the inserts 6 may be formed as capsules or the like without any duct 12, nozzle 13 or the like. Instead, each insert 6 is connected individually to a gas supply and to a common outlet arrangement, such as a duct 12, nozzle 13 or the like for dispensing the respective dose of the formulation 2.

According to another embodiment, a secondary packaging may be used for packing and protecting the storage device 4/carrier 5, in particular, for storage purposes before inserting the storage device 4/carrier 5 into the dispensing device 1. Additionally the whole device 1 including storage device 4/carrier 5 may be stored in a secondary water vapor proof packaging.

According to a further embodiment, the dispensing devise 1 may be breath activated, in particular, wherein the formulation 2 is only released after the patient's or user's inhalation rate has reached a predetermined level, preferably by the use of a pressure sensitive means, such as a bursting element, membrane or valve, or any other mechanism.

In the following, two examples are described which show the effect of the preferred inserts 6 with ducts 12.

EXAMPLE 1

A blend of 90.0% by weight of lactose 200, of 9.7% by weight of fine lactose, and of 0.3% by weight of Tiotropium was used. The mean particle diameter of lactose 200 was about 45 µm, of fine lactose about 4 µm and of Tiotropium about 4 µm. About 5.5 mg of the blend was positioned as powder in the storage 10 which had a substantially cylindrical shape with a diameter of 3 mm and an axial length of 3 mm. 5 ml of compressed air was supplied into the chamber 10 with a gauge pressure of about 100 kPa. The powder was dispensed via duct 12 of substantially rectangular cross section having a smallest side of about 0.18 mm and a largest side of about 1.5 mm. The duct 12 divided into two duct sections 12a, 12b (in particular, as shown in FIG. 9), wherein each section had a substantially rectangular cross section with a smallest side of about 0.18 mm and the largest side of about 0.75 mm. The total length of the duct 12 including the sections 12a, 12b was about 8 mm. The result was that 100% of the metered mass, i.e. all powder in chamber 10, was dispensed. Approximately 50% of the Tiotropium was measured as fine fraction on an Anderson Cascade Impactor at both 30 and 60 l/min.

EXAMPLE 2

About 1.5 mg of Fenoterol with a mean particle diameter of 4 µm was positioned as powder in the storage chamber 10 which had a substantially cylindrical shape with a diameter of 2 mm and an axial length of 2 mm. 5 ml of compressed air was supplied via the gas inlet having an inlet orifice of 0.5 mm into the chamber 10 with a gauge pressure of about 150 kPa. The powder was dispensed via a duct 12 of substantially rectangular cross section having a smallest side of 0.075 mm and a largest side of 1.5 mm. The duct 12 divided into two duct sections 12a, 12b (in particular, as shown in FIG. 9), wherein each section had a substantially rectangular cross section with a smallest side of about 0.075 mm and the largest side of about 0.75 mm. The total length of the channel including the sections 12a, 12b was about 8 mm. The result was that 100% of the metered mass, i.e., all powder in chamber 10, was dispensed. Approximately 45% of the Fenoterol was measured as fine fraction on an Anderson Cascade Impactor at both 30 and 60 l/min.

The formulation may contain or comprise additional pharmacologically active substances or mixtures of substances, preferably selected from those groups:

The below mentioned compounds may be used on their own or combined with other active substances for use in the device according to this invention. These include, in particular, betamimetics, anticholinergics, corticosteroids, PDE4-inhibitors, LTD4-antagonists, EGFR-inhibitors, dopamin-agonists, antiallergic agents, PAF-antagonists und PI3-kinase inhibitors, but also combinations of two or three active substances, i.e.:

Betamimetics with corticosteroids, PDE4-inhibitors, EGFR-inhibitors or LTD4-antagonists, Anticholinergics with betamimetics, corticosteroids, PDE4-inhibitors, EGFR-inhibitors or LTD4-antagonists, Corticosteroids with PDE4-inhibitors, EGFR-inhibitors or LTD4-antagonists PDE4-inhibitors with EGFR-inhibitors or LTD4-antagonists EGFR-inhibitors with LTD4-antagonists.

Examples of preferred betamimetics which may be mentioned include Albuterole, Arformoterole, Bambuterole, Bitolterole, Broxaterole, Carbuterole, Clenbuterole, Fenoterole, Formoterole, Hexoprenaline, Ibuterole, Isoetharine, Isoprenaline, Levosalbutamole, Mabuterole, Meluadrine, Metaproterenole, Orciprenaline, Pirbuterole, Procaterole, Reproterole, Rimiterole, Ritodrine, Salmefamole, Salmeterole, Soterenole, Sulphonterole, Terbutaline, Tiaramide, Tolubuterole, Zinterole, CHF-1035, HOKU-81, KUL-1248 and

- 3-(4-{6-[2-Hydroxy-2-(4-hydroxy-3-hydroxymethyl-phenyl)-ethylamino]-hexyloxy}-butyl)-benzyl-sulfonamide
- 5-[2-(5,6-Diethyl-indan-2-ylamino)-1-hydroxy-ethyl]-8-hydroxy-1H-quinolin-2-one
- 4-Hydroxy-7-[2-{[2-{[3-(2-phenylethoxy)propyl]sulphonyl}ethyl]-amino}ethyl]-2(3H)-benzothiazolone
- 1-(2-Fluoro-4-hydroxyphenyl)-2-[4-(1-benzimidazolyl)-2-methyl-2-butylamino]ethanole
- 1-[3-(4-Methoxybenzyl-amino)-4-hydroxyphenyl]-2-[4-(1-benzimidazolyl)-2-methyl-2-butylamino]ethanole
- 1-[2H-5-hydroxy-3-oxo-4H-1,4-benzoxazin-8-yl]-2-[3-(4-N,N-dimethylaminophenyl)-2-methyl-2-propylamino]ethanole
- 1-[2H-5-hydroxy-3-oxo-4H-1,4-benzoxazin-8-yl]-2-[3-(4-methoxyphenyl)-2-methyl-2-propylamino]ethanole
- 1-[2H-5-hydroxy-3-oxo-4H-1,4-benzoxazin-8-yl]-2-[3-(4-n-butyloxyphenyl)-2-methyl-2-propylamino]ethanole
- 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol
- 5-Hydroxy-8-(1-hydroxy-2-isopropylaminobutyl)-2H-1,4-benzoxazin-3-(4H)-one
- 1-(4-Amino-3-chloro-5-trifluormethylphenyl)-2-tert.-butylamino)ethanol
- 6-Hydroxy-8-{1-hydroxy-2-[2-(4-methoxy-phenyl)-1,1-dimethyl-ethylamino]-ethyl}-4H-benzo[1,4]oxazin-3-one
- 6-Hydroxy-8-{1-hydroxy-2-[2-(4-phenoxy-acetic acid ethylester)-1,1-dimethyl-ethylamino]-ethyl}-4H-benzo[1,4]oxazin-3-one
- 6-Hydroxy-8-{1-hydroxy-2-[2-(4-phenoxy-acetic acid)-1,1-dimethyl-ethylamino]-ethyl}-4H-benzo[1,4]oxazin-3-one
- 8-{2-[1,1-Dimethyl-2-(2,4,6-trimethylphenyl)-ethylamino]-1-hydroxy-ethyl}-6-hydroxy-4H-benzo[1,4]oxazin-3-one
- 6-Hydroxy-8-{1-hydroxy-2-[2-(4-hydroxy-phenyl)-1,1-dimethyl-ethylamino]-ethyl}-4H-benzo[1,4]oxazin-3-one
- 6-Hydroxy-8-{1-hydroxy-2-[2-(4-isopropyl-phenyl)-1,1 dimethyl-ethylamino]-ethyl}-4H-benzo[1,4]oxazin-3-one
- 8-{2-[2-(4-Ethyl-phenyl)-1,1-dimethyl-ethylamino]-1-hydroxy-ethyl}-6-hydroxy-4H-benzo[1,4]oxazin-3-one
- 8-{2-[2-(4-Ethoxy-phenyl)-1,1-dimethyl-ethylamino]-1-hydroxy-ethyl}-6-hydroxy-4H-benzo[1,4]oxazin-3-one
- 4-(4-{2-[2-Hydroxy-2-(6-hydroxy-3-oxo-3,4-dihydro-2H-benzo[1,4]oxazin-8-yl)-ethylamino]-2-methyl-propyl}-phenoxy)-butyric acid
- 8-{2-[2-(3,4-Difluor-phenyl)-1,1-dimethyl-ethylamino]-1-hydroxy-ethyl}-6-hydroxy-4H-benzo[1,4]oxazin-3-on
- 1-(4-Ethoxy-carbonylamino-3-cyano-5-fluorophenyl)-2-(tert.-butylamino)ethanol
- 2-Hydroxy-5-(1-hydroxy-2-{2-[4-(2-hydroxy-2-phenyl-ethylamino)-phenyl]-ethylamino}-ethyl)-benzaldehyde
- N-[2-Hydroxy-5-(1-hydroxy-2-{2-[4-(2-hydroxy-2-phenyl-ethylamino)-phenyl]-ethylamino}-ethyl)-phenyl]-formamide
- 8-Hydroxy-5-(1-hydroxy-2-{2-[4-(6-methoxy-biphenyl-3-ylamino)-phenyl]-ethylamino}-ethyl)-1H-quinolin-2-one
- 8-Hydroxy-5-[1-hydroxy-2-(6-phenethylamino-hexylamino)-ethyl]-1H-quinolin-2-one
- 5-[2-(2-{4-[4-(2-Amino-2-methyl-propoxy)-phenylamino]-phenyl}-ethylamino)-1-hydroxy-ethyl]-8-hydroxy-1H-quinolin-2-one
- [3-(4-{6-[2-Hydroxy-2-(4-hydroxy-3-hydroxymethyl-phenyl)-ethylamino]-hexyloxy}-butyl)-5-methyl-phenyl]-urea
- 4-(2-{6-[2-(2,6-Dichloro-benzyloxy)-ethoxy]-hexylamino}-1-hydroxy-ethyl)-2-hydroxymethyl-phenol
- 3-(4-{6-[2-Hydroxy-2-(4-hydroxy-3-hydroxymethyl-phenyl)-ethylamino]-hexyloxy}-butyl)-benzenesulfonamide
- 3-(3-{7-[2-Hydroxy-2-(4-hydroxy-3-hydroxymethyl-phenyl)-ethylamino]-heptyloxy}-propyl)-benzenesulfonamide
- 4-(2-{6-[4-(3-Cyclopentanesulfonyl-phenyl)-butoxy]-hexylamino}-1-hydroxy-ethyl)-2-hydroxymethyl-phenol
- N-Adamantan-2-yl-2-(3-{2-[2-hydroxy-2-(4-hydroxy-3-hydroxymethyl-phenyl)-ethylamino]-propyl}-phenyl)-acetamide optionally in racemic form, as enantiomers, diastereomeres or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate und hydro-p-toluenesulfonate.

Examples of preferred anticholinergics which may be mentioned include Tiotropium salts, preferred the bromide salt, Oxitropium salts, preferred the bromide salt, Flutropium salts, preferred the bromide salt, Ipratropium salts, preferred the bromide salt, Glycopyrronium salts, preferred the bromide salt, Trospium salts, preferred the chloride salt, Tolterodin. From the above mentioned salts the pharmacologically active part is the cation, possible anions are chloride, bromide, iodide, sulfate, phosphate, methansulfonate, nitrate, maleate, acetate, citrate, fumarate, tartrate, oxalate, succinate, benzoate oder p-toluenesulfonate. Furthermore:

- 2,2-Diphenylpropion acid tropenolester-methobromide
- 2,2-Diphenylpropion acid scopinester-methobromide
- 2-Fluor-2,2-Diphenylacetic acid scopinester-methobromide
- 2-Fluor-2,2-Diphenylacetic acid tropenolester-methobromide
- 3,3',4,4'-Tetrafluorbenzil acid tropenolester-Methobromide
- 3,3',4,4'-Tetrafluorbenzil acid scopinester-Methobromide
- 4,4'-Difluorbenzil acid tropenolester-Methobromide
- 4,4'-Difluorbenzil acid scopinester-Methobromide
- 3,3'-Difluorbenzil acid tropenolester-Methobromide
- 3,3'-Difluorbenzil acid scopinester-Methobromide
- 9-Hydroxy-fluoren-9-carbon acid tropenolester -Methobromide
- 9-Fluor-fluoren-9-carbon acid tropenolester -Methobromide
- 9-Hydroxy-fluoren-9-carbon acid scopinester -Methobromide
- 9-Fluor-fluoren-9-carbon acid scopinester Methobromide 9-Methyl-fluoren-9-carbon acid tropenolesterMethobromide
9-Methyl-fluoren-9-carbon acid scopinesterMethobromide
Benzil acid cyclopropyltropinester-Methobromide
2,2-Diphenylpropion acid cyclopropyltropinester-Methobromide
9-Hydroxy-xanthen-9-carbon acid cyclopropyltropinesterMethobromide
9-Methyl-fluoren-9-carbon acid cyclopropyltropinester-Methobromide
9-Methyl-xanthen-9-carbon acid cyclopropyltropinester-Methobromide
9-Hydroxy-fluoren-9-carbon acid cyclopropyltropinester - Methobromide
4,4'-Difluorbenzil acid methylestercyclopropyltropinester-Methobromide
9-Hydroxy-xanthen-9-carbon acid tropenolester-Methobromide
9-Hydroxy-xanthen-9-carbon acid scopinester Methobromide
9-Methyl-xanthen-9-carbon acid tropenolester-Methobromide
9-Methyl-xanthen-9-carbon acid scopinesterMethobromide
9-Ethyl-xanthen-9-carbon acid tropenolester Methobromide
9-Difluormethyl-xanthen-9-carbon acid tropenolester - Methobromide
9-Hydroxymethyl-xanthen-9-carbon acid scopinester - Methobromide Examples of preferred corticosteroids which may be mentioned include Beclomethasone, Betamethasone, Budesonide, Butixocorte, Ciclesonide, Deflazacorte, Dexamethasone, Etiprednole, Flunisolide, Fluticasone, Loteprednole, Mometasone, Prednisolone, Prednisone, Rofleponide, Triamcinolone, RPR-106541, NS-126, ST-26 and 6,9-Difluoro-17-[(2-furanylcarbonyl)oxy]-1,1-hydroxy-16-methyl-3-oxo-androsta-1,4-dien-17-carbothion acid (S)-fluoromethylester 6,9-Difluoro-11-hydroxy-16-methyl-3-oxo-17-propionyloxy-androsta-1,4-dien-17-carbothion acid (S)-(2-oxo-tetrahydro-furan-3S-yl)ester, 6☐,9☐-difluoro-11☐-hydroxy-16☐-methyl-3-oxo-17☐-(2,2,3,3-tertamethylcyclopropylcarbonyl)oxy-androsta-1,4-diene-17☐-carboxylic acid cyanomethyl ester optionally in racemic form, as enantiomers, diastereomeres or as pharmacologically acceptable salts, solvates or hydrates. Examples for preferred salts and derivatives are alkali salts, i.e., sodium or potassium salts, sulfobenzoates, phosphates, isonicotinates, acetates, dichloroacetates, propionates, dihydrogenphosphates, palmitates, pivalates or furoates.

Examples of preferred PDE4-inhibitors which may be mentioned include Enprofylline, Theophylline, Roflumilaste, Ariflo (Cilomilast), Tofimilaste, Pumafentrine, Lirimilaste, Arofylline, Atizorame, D-4418, Bay-198004, BY343, CP-325,366, D-4396 (Sch-351591), AWD-12-281 (GW-842470), NCS-613, CDP-840, D-4418, PD-168787, T-440, T-2585, V-11294A, Cl-1018, CDC-801, CDC-3052, D-22888, YM-58997, Z-15370 and N-(3,5-Dichloro-1-oxo-pyridin-4-yl)-4-difluoromethoxy-3-cyclopropylmethoxy-benzamide (−)p-[(4aR*,10bS*)-9-Ethoxy-1,2,3,4,4a,10b-hexahydro-8-methoxy-2-methylbenzo[s][1,6]naphthyridin-6-yl]-N,N-diisopropylbenzamid (R)-(+)-1-(4-Bromobenzyl)-4-[(3-cyclopentyloxy)-4-methoxyphenyl]-2-pyrrolidon 3-(Cyclopentyloxy-4-methoxyphenyl)-1-(4-N'-[N-2-cyano-S-methyl-isothioureido]benzyl)-2-pyrrolidone cis[4-Cyano-4-(3-cyclopentyloxy-4-methoxyphenyl)cyclohexan-1-carbon acid]

2-carbomethoxy-4-cyano-4-(3-cyclopropylmethoxy-4-difluoromethoxyphenyl)cyclohexan-1-one cis[4-Cyano-4-(3-cyclopropylmethoxy-4-difluoromethoxyphenyl)cyclohexan-1-ol]

(R)-(+)-Ethyl [4-(3-cyclopentyloxy-4-methoxyphenyl)pyrrolidin-2-yliden]acetate (S)-(−)-Ethyl[4-(3-cyclopentyloxy-4-methoxyphenyl)pyrrolidin-2-yliden]acetate 9-Cyclopentyl-5,6-dihydro-7-ethyl-3-(2-thienyl)-9H-pyrazolo[3,4-c]-1,2,4-triazolo[4,3-a]pyridine 9-Cyclopentyl-5,6-dihydro-7-ethyl-3-(tert-butyl)-9H-pyrazolo[3,4-c]-1,2,4-triazolo[4,3-a]pyridine optionally in racemic form, as enantiomers, diastereomeres or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate und hydro-p-toluenesulfonate.

Examples of preferred LTD4-antagonists which may be mentioned include Montelukaste, Pranlukaste, Zafirlukaste, MCC-847 (ZD-3523), MN-001, MEN-91507 (LM-1507), VUF-5078, VUF-K-8707, L-733321 and 1-(((R)-(3-(2-(6,7-Difluoro-2-quinolinyl)ethenyl)phenyl)-3-(2-(2-hydroxy-2-propyl)phenyl)thio)methylcyclopropane-acetic acid, 1-(((1R)-3(3-(2-(2,3-Dichlorothieno[3,2-b]pyridin-5-yl)-(E)-ethenyl)phenyl)-3-(2-(1-hydroxy-1-methylethyl)phenyl)propyl)thio)methyl)cyclopropane acetic acid

[2-[[2-(4-tert-Butyl-2-thiazolyl)-5-benzofuranyl]oxymethyl]phenyl]acetic acid optionally in racemic form, as enantiomers, diastereomeres or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate und hydro-p-toluenesulfonate. Further examples for optionally preferred salts and derivatives are alkali salts, i.e., sodium or potassium salts, sulfobenzoates, phosphates, isonicotinates, acetates, propionates, dihydrogenphosphates, palmitates, pivalates or furoates.

Examples of preferred EGFR-inhibitors which may be mentioned include Cetuximabe, Trastuzumabe, ABX-EGF, Mab ICR-62 and 4-[(3-Chlor-4-fluorphenyl)amino]-6-{[4-(morpholin-4-yl)-1-oxo-2-buten-1-yl]amino}-7-cyclopropylmethoxy-chinazoline 4-[(3-Chlor-4-fluorphenyl)amino]-6-{[4-(N,N-diethylamino)-1-oxo-2-buten-1-yl]-amino}-7-cyclopropylmethoxy-chinazoline 4-[(3-Chlor-4-fluorphenyl)amino]-6-{[4-(N,N-dimethylamino)-1-oxo-2-buten-1-yl]amino}-7-cyclopropylmethoxy-chinazoline 4-[(R)-(1-Phenyl-ethyl)amino]-6-{[4-(morpholin-4-yl)-1-oxo-2-buten-1-yl]amino}-7-cyclopentyloxy-chinazoline 4-[(3-Chlor-4-fluor-phenyl)amino]-6-{[4-((R)-6-methyl-2-oxo-morpholin-4-yl)-1-oxo-2-buten-1-yl]amino}-7-cyclopropylmethoxy-chinazoline 4-[(3-Chlor-4-fluor-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-chinazoline 4-[(3-Chlor-4-fluor-phenyl)amino]-6-{[4-((R)-2-methoxymethyl-6-oxo-morpholin-4-yl)-1-oxo-2-buten-1-yl]amino}-7-cyclopropylmethoxy-chinazoline 4-[(3-Chlor-4-fluor-phenyl)amino]-6-[2-((S)-6-methyl-2-oxo-morpholin-4-yl)-ethoxy]-7-methoxy-chinazoline 4-[(3-Chlor-4-fluorphenyl)amino]-6-({4-[N-(2-methoxy-ethyl)-N-methyl-amino]-1-oxo-2-buten-1-yl}amino)-7-cyclopropylmethoxy-chinazoline 4-[(3-Chlor-4-fluorphenyl)amino]-6-{[4-(N,N-dimethylamino)-1-oxo-2-buten-1-yl]amino}-7-cyclopentyloxy-chinazoline 4-[(R)-(1-Phenyl-ethyl)amino]-6-{[4-(N,N-bis-(2-methoxy-ethyl)-amino]-1-oxo-2-buten-1-yl]amino}-7-cyclopropylmethoxy-chinazoline 4-[(R)-(1-Phenyl-ethyl)amino]-6-({4-[N-(2-methoxy-ethyl)-N-ethyl-amino]-1-oxo-2-buten-1-yl}amino)-7-cyclopropylmethoxy-chinazoline 4-[(R)-(1-Phenyl-ethyl)amino]-6-({4-[N-(2-methoxy-ethyl)-N-methyl-amino]-1-oxo-2-buten-1-yl}amino)-7-cyclopropylmethoxy-chinazoline 4-[(R)-(1-Phenyl-ethyl)amino]-6-({4-[N-(tetrahydropyran-4-yl)-N-methyl-amino]-1-oxo-2-buten-1-yl}amino)-7-cyclopropylmethoxy-chinazoline 4-[(3-Chlor-4-fluorphenyl)amino]-6-{[4-(N,N-dimethylamino)-1-oxo-2-buten-1-yl]amino}-7-((R)-tetrahydrofuran-3-yloxy)-chinazoline 4-[(3-Chlor-4-fluorphenyl)amino]-6-{[4-(N,N-dimethylamino)-1-oxo-2-buten-1-yl]amino}-7-((S)-tetrahydrofuran-3-yloxy)-chinazoline 4-[(3-Chlor-4-fluorphenyl)amino]-6-({4-[N-(2-methoxy-ethyl)-N-methyl-amino]-1-oxo-2-buten-1-yl}amino)-7-cyclopentyloxy-chinazoline 4-[(3-Chlor-4-fluorphenyl)amino]-6-{[4-(N-cyclopropyl-N-methyl-amino)-1-oxo-2-buten-1-yl]amino}-7-cyclopentyloxy-chinazoline 4-[(3-Chlor-4-fluorphenyl)amino]-6-{[4-(N,N-dimethylamino)-1-oxo-2-buten-1-yl]amino}-7-[(R)-(tetrahydrofuran-2-yl)methoxy]-chinazoline 4-[(3-Chlor-4-fluorphenyl)amino]-6-{[4-(N,N-dimethylamino)-1-oxo-2-buten-1-yl]amino}-7-[(S)-(tetrahydrofuran-2-yl)methoxy]-chinazoline 4-[(3-Ethinyl-phenyl)amino]-6,7-bis-(2-methoxy-ethoxy)-chinazoline 4-[(3-Chlor-4-fluorphenyl)amino]-7-[3-(morpholin-4-yl)-propyloxy]-6-[(vinyl-carbonyl)amino]-chinazoline 4-[(R)-(1-Phenyl-ethyl)amino]-6-(4-hydroxy-phenyl)-7H-pyrrolo[2,3-d]pyrimidine 3-Cyano-4-[(3-chlor-4-fluorphenyl)amino]-6-{[4-(N,N-dimethylamino)-1-oxo-2-buten-1-yl]amino}-7-ethoxy-chinoline 4-{[3-Chlor-4-(3-fluor-benzyloxy)-phenyl]amino}-6-(5-{[(2-methansulfonyl-ethyl)amino]methyl}-furan-2-yl)chinazoline 4-[(R)-(1-Phenyl-ethyl)amino]-6-{[4-((R)-6-methyl-2-oxo-morpholin-4-yl)-1-oxo-2-buten-1-yl]amino}-7-methoxy-chinazoline 4-[(3-Chlor-4-fluorphenyl)amino]-6-{[4-(morpholin-4-yl)-1-oxo-2-buten-1-yl]amino}-7-[(tetrahydrofuran-2-yl)methoxy]-chinazoline 4-[(3-Chlor-4-fluorphenyl)amino]-6-({4-[N,N-bis-(2-methoxy-ethyl)-amino]-1-oxo-2-buten-1-yl}amino)-7-[(tetrahydrofuran-2-yl)methoxy]-chinazoline 4-[(3-Ethinyl-phenyl)amino]-6-{[4-(5,5-dimethyl-2-oxo-morpholin-4-yl)-1-oxo-2-buten-1-yl]amino}-chinazoline 4-[(3-Chlor-4-fluor-phenyl)amino]-6-[2-(2,2-dimethyl-6-oxo-morpholin-4-yl)-ethoxy]-7-methoxy-chinazoline 4-[(3-Chlor-4-fluor-phenyl)amino]-6-[2-(2,2-dimethyl-6-oxo-morpholin-4-yl)-ethoxy]-7-[(R)-(tetrahydrofuran-2-yl)methoxy]-chinazoline 4-[(3-Chlor-4-fluor-phenyl)amino]-7-[2-(2,2-dimethyl-6-oxo-morpholin-4-yl)-ethoxy]-6-[(S)-(tetrahydrofuran-2-yl)methoxy]-chinazoline 4-[(3-Chlor-4-fluor-phenyl)amino]-6-{2-[4-(2-oxo-morpholin-4-yl)-piperidin-1-yl]-ethoxy}-7-methoxy-chinazoline 4-[(3-Chlor-4-fluor-phenyl)amino]-6-[1-(tert.-butyloxycarbonyl)-piperidin-4-yloxy]-7-methoxy-chinazoline 4-[(3-Chlor-4-fluor-phenyl)amino]-6-(trans-4-amino-cyclohexan-1-yloxy)-7-methoxy-chinazoline 4-[(3-Chlor-4-fluor-phenyl)amino]-6-(trans-4-methansulfonylamino-cyclohexan-1-yloxy)-7-methoxy-chinazoline 4-[(3-Chlor-4-fluor-phenyl)amino]-6-(tetrahydropyran-3-yloxy)-7-methoxy-chinazoline 4-[(3-Chlor-4-fluor-phenyl)amino]-6-(1-methyl-piperidin-4-yloxy)-7-methoxy-chinazoline 4-[(3-Chlor-4-fluor-phenyl)amino]-6-{1-[(morpholin-4-yl)carbonyl]-piperidin-4-yloxy}-7-methoxy-chinazoline 4-[(3-Chlor-4-fluor-phenyl)amino]-6-{1-[(methoxymethyl)carbonyl]-piperidin-4-yloxy}-7-methoxy-chinazoline 4-[(3-Chlor-4-fluor-phenyl)amino]-6-(piperidin-3-yloxy)-7-methoxy-chinazoline 4-[(3-Chlor-4-fluor-phenyl)amino]-6-[1-(2-acetylamino-ethyl)-piperidin-4-yloxy]-7-methoxy-chinazoline 4-[(3-Chlor-4-fluor-phenyl)amino]-6-(tetrahydropyran-4-yloxy)-7-ethoxy-chinazoline 4-[(3-Chlor-4-fluor-phenyl)amino]-6-((S)-tetrahydrofuran-3-yloxy)-7-hydroxy-chinazoline 4-[(3-Chlor-4-fluor-phenyl)amino]-6-(tetrahydropyran-4-yloxy)-7-(2-methoxy-ethoxy)-chinazoline 4-[(3-Chlor-4-fluor-phenyl)amino]-6-{trans-4-[(dimethylamino)sulfonylamino]-cyclohexan-1-yloxy}-7-methoxy-chinazoline 4-[(3-Chlor-4-fluor-phenyl)amino]-6-{trans-4-[(morpholin-4-yl)carbonylamino]-cyclohexan-1-yloxy}-7-methoxy-chinazoline 4-[(3-Chlor-4-fluor-phenyl)amino]-6-{trans-4-[(morpholin-4-yl)sulfonylamino]-cyclohexan-1-yloxy}-7-methoxy-chinazoline 4-[(3-Chlor-4-fluor-phenyl)amino]-6-(tetrahydropyran-4-yloxy)-7-(2-acetylamino-ethoxy)-chinazoline 4-[(3-Chlor-4-fluor-phenyl)amino]-6-(tetrahydropyran-4-yloxy)-7-(2-methansulfonylamino-ethoxy)-chinazoline 4-[(3-Chlor-4-fluor-phenyl)amino]-6-{1-[(piperidin-1-yl)carbonyl]-piperidin-4-yloxy}-7-methoxy-chinazoline 4-[(3-Chlor-4-fluor-phenyl)amino]-6-(1-aminocarbonylmethyl-piperidin-4-yloxy)-7-methoxy-chinazoline 4-[(3-Chlor-4-fluor-phenyl)amino]-6-(cis-4-{N-[(tetrahydropyran-4-yl)carbonyl]-N-methylamino}-cyclohexan-1-yloxy)-7-methoxy-chinazoline 4-[(3-Chlor-4-fluor-phenyl)amino]-6-(cis-4-{N-[(morpholin-4-yl)carbonyl]-N-methyl-amino}-cyclohexan-1-yloxy)-7-methoxy-chinazoline 4-[(3-Chlor-4-fluor-phenyl)amino]-6-(cis-4-{N-[(morpholin-4-yl)sulfonyl]-N-methyl-amino}-cyclohexan-1-yloxy)-7-methoxy-chinazoline 4-[(3-Chlor-4-fluor-phenyl)amino]-6-(trans-4-ethansulfonylamino-cyclohexan-1-yloxy)-7-methoxy-chinazoline 4-[(3-Chlor-4-fluor-phenyl)amino]-6-(1-methansulfonyl-piperidin-4-yloxy)-7-ethoxy-chinazoline 4-[(3-Chlor-4-fluor-phenyl)amino]-6-(1-methansulfonyl-piperidin-4-yloxy)-7-(2-methoxy-ethoxy)-chinazoline 4-[(3-Chlor-4-fluor-phenyl)amino]-6-[1-(2-methoxy-acetyl)-piperidin-4-yloxy]-7-(2-methoxy-ethoxy)-chinazoline 4-[(3-Chlor-4-fluor-phenyl)amino]-6-(cis-4-acetylamino-cyclohexan-1-yloxy)-7-methoxy-chinazoline 4-[(3-Ethinyl-phenyl)amino]-6-[1-(tert.-butyloxycarbonyl)-piperidin-4-yloxy]-7-methoxy-chinazoline 4-[(3-Ethinyl-phenyl)amino]-6-(tetrahydropyran-4-yloxy)-7-methoxy-chinazoline 4-[(3-Chlor-4-fluor-phenyl)amino]-6-(cis-4-{N-[(piperidin-1-yl)carbonyl]-N-methyl-amino}-cyclohexan-1-yloxy)-7-methoxy-chinazoline 4-[(3-Chlor-4-fluor-phenyl)amino]-6-(cis-4-{N-[(4-methyl-piperazin-1-yl)carbonyl]-N-methyl-amino}-cyclohexan-1-yloxy)-7-methoxy-chinazoline 4-[(3-Chlor-4-fluor-phenyl)amino]-6-{cis-4-[(morpholin-4-yl)carbonylamino]-cyclohexan-1-yloxy}-7-methoxy-chinazoline 4-[(3-Chlor-4-fluor-phenyl)amino]-6-{1-[2-(2-oxopyrrolidin-1-yl)ethyl]-piperidin-4-yloxy}-7-methoxy-chinazoline 4-[(3-Chlor-4-fluor-phenyl)amino]-6-{1-[(morpholin-4-yl)carbonyl]-piperidin-4-yloxy}-7-(2-methoxy-ethoxy)-chinazoline 4-[(3-Ethinyl-phenyl)amino]-6-(1-acetyl-piperidin-4-yloxy)-7-methoxy-chinazoline 4-[(3-Ethinyl-phenyl)amino]-6-(1-methyl-piperidin-4-yloxy)-7-methoxy-chinazoline 4-[(3-Ethinyl-phenyl)amino]-6-(1-methansulfonyl-piperidin-4-yloxy)-7-methoxy-chinazoline 4-[(3-Chlor-4-fluor-phenyl)amino]-6-(1-methyl-piperidin-4-yloxy)-7(2-methoxy-ethoxy)-chinazoline 4-[(3-Chlor-4-fluor-phenyl)amino]-6-(1-isopropyloxycarbonyl-piperidin-4-yloxy)-7-methoxy-chinazoline 4-[(3-Chlor-4-fluor-phenyl)amino]-6-(cis-4-methylamino-cyclohexan-1-yloxy)-7-methoxy-chinazoline 4-[(3-Chlor-4-fluor-phenyl)amino]-6-{cis-4-[N-(2-methoxy-acetyl)-N-methyl-amino]-cyclohexan-1-yloxy}-7-methoxy-chinazoline 4-[(3-Ethinyl-phenyl)amino]-6-(piperidin-4-yloxy)-7-methoxy-chinazoline 4-[(3-Ethinyl-phenyl)amino]-6-[1-(2-methoxy-acetyl)-piperidin-4-yloxy]-7-methoxy-chinazoline 4-[(3-Ethinyl-phenyl)amino]-6-{1-[(morpholin-4-yl)carbonyl]-piperidin-4-yloxy}-7-methoxy-chinazoline 4-[(3-Chlor-4-fluor-phenyl)amino]-6-{1-[(cis-2,6-dimethyl-morpholin-4-yl)carbonyl]-piperidin-4-yloxy}-7-methoxy-chinazoline 4-[(3-Chlor-4-fluor-phenyl)amino]-6-{1-[(2-methyl-morpholin-4-yl)carbonyl]-piperidin-4-yloxy}-7-methoxy-chinazoline 4-[(3-Chlor-4-fluor-phenyl)amino]-6-{1-[(S,S)-(2-oxa-5-aza-bicyclo[2.2.1]hept-5-yl)carbonyl]-piperidin-4-yloxy}-7-methoxy-chinazoline 4-[(3-Chlor-4-fluor-phenyl)amino]-6-{1-[(N-methyl-N-2-methoxyethyl-amino)carbonyl]-piperidin-4-yloxy}-7-methoxy-chinazoline 4-[(3-Chlor-4-fluor-phenyl)amino]-6-(1-ethyl-piperidin-4-yloxy)-7-methoxy-chinazoline 4-[(3-Chlor-4-fluor-phenyl)amino]-6-{1-[(2-methoxyethyl)carbonyl]-piperidin-4-yloxy}-7-methoxy-chinazoline 4-[(3-Chlor-4-fluor-phenyl)amino]-6-{1-[(3-methoxypropyl-amino)-carbonyl]-piperidin-4-yloxy}-7-methoxy-chinazoline 4-[(3-Chlor-4-fluor-phenyl)amino]-6-[cis-4-(N-methansulfonyl-N-methyl-amino)-cyclohexan-1-yloxy]-7-methoxy-chinazoline 4-[(3-Chlor-4-fluor-phenyl)amino]-6-[cis-4-(N-acetyl-N-methyl-amino)-cyclohexan-1-yloxy]-7-methoxy-chinazoline 4-[(3-Chlor-4-fluor-phenyl)amino]-6-(trans-4-methylamino-cyclohexan-1-yloxy)-7-methoxy-chinazoline 4-[(3-Chlor-4-fluor-phenyl)amino]-6-[trans-4-(N-methansulfonyl-N-methyl-amino)-cyclohexan-1-yloxy]-7-methoxy-chinazoline 4-[(3-Chlor-4-fluor-phenyl)amino]-6-(trans-4-dimethylamino-cyclohexan-1-yloxy)-7-methoxy-chinazoline 4-[(3-Chlor-4-fluor-phenyl)amino]-6-(trans-4-{N-[(morpholin-4-yl)carbonyl]-N-methyl-amino}-cyclohexan-1-yloxy)-7-methoxy-chinazoline 4-[(3-Chlor-4-fluor-phenyl)amino]-6-[2-(2,2-dimethyl-6-oxo-morpholin-4-yl)-ethoxy]-7-[(S)-(tetrahydrofuran-2-yl)methoxy]-chinazoline 4-[(3-Chlor-4-fluor-phenyl)amino]-6-(1-methansulfonyl-piperidin-4-yloxy)-7-methoxy-chinazoline 4-[(3-Chlor-4-fluor-phenyl)amino]-6-(1-cyano-piperidin-4-yloxy)-7-methoxy-chinazoline optionally in racemic form, as enantiomers, diastereomeres or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate und hydro-p-toluenesulfonate.

Examples of preferred dopamin antagonists which may be mentioned include Bromocriptine, Cabergoline, Alpha-Dihydroergocryptine, Lisuride, Pergolide, Pramipexole, Roxindole, Ropinirole, Talipexole, Terguride and Viozane, optionally in racemic form, as enantiomers, diastereomeres or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate und hydro-p-toluenesulfonate.

Examples of preferred antiallergic agents which may be mentioned include Epinastine, Cetirizine, Azelastine, Fexofenadine, Levocabastine, Loratadine, Mizolastine, Ketotifene, Emedastine, Dimetindene, Clemastine, Bamipine, Cexchlorpheniramine, Pheniramine, Doxylamine, Chlorphenoxamine, Dimenhydrinate, Diphenhydramine, Promethazine, Ebastine, Desloratidine and Meclozine, optionally in racemic form, as enantiomers, diastereomeres or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate und hydro-p-toluenesulfonate.

Moreover, inhalable macromolecules can be used as pharmacologically active substances, as disclosed in European Patent Application EP 1 003 478 A1 or Canadian Patent Application CA 2297174 A1.

Moreover, the compound could be from the group of derivates of ergotalcaloids, triptane, CGRP-antagonists, phosphodiesterase-V-inhibitores, optionally in the form of the racemates, the enantiomers, the diastereomers and optionally the pharmacologically acceptable acid addition salts and the hydrates thereof.

As derivates of alkaloides: dihydroergotamine, ergotamine.

What is claimed is:

1. Dispensing device for dispensing a medical formulation as a spray of fine particles, the dispensing device comprising multiple separate and pre-metered doses of the formulation, wherein the dispensing device comprises a carrier with multiple inserts, at least some of the inserts containing a single dose of the formulation and means for individually dispensing the formulation from the respective insert; wherein each insert comprises a gas inlet at one end of each insert, a gas outlet at an opposite end of each insert, and a storage chamber between the gas inlet and gas outlet that is substantially circular in cross section viewed in a direction transverse of a direction from the gas inlet toward the gas outlet, the gas inlet being tangentially connected to the storage chamber to generate swirls of the formulation.

2. Dispensing device according to claim 1, wherein the formulation is a liquid.

3. Dispensing device according to claim 1, wherein the formulation is a powder.

4. Dispensing device according to claim 1, wherein each insert is located in a respective cavity of the carrier and wherein each insert can be moved or pushed at least partially out of its cavity.

5. Dispensing device according to claim 4, wherein each insert can be pushed through a respective sealing of the respective cavity for opening the sealing.

6. Dispensing device according to claim 1, wherein the carrier is one of a molded element, a ring, a strip, a cartridge, a blister, and a container.

7. Dispensing device according to claim 1, wherein the carrier is flexible and forms a belt.

8. Dispensing device according to claim 1, wherein the carrier forms stiff guides for the inserts.

9. Dispensing device according to claim 1, wherein the dispensing device comprises at least one of a common duct, nozzle and mouthpiece.

10. Dispensing device according to claim 1, wherein each insert comprises a jet impinging means for impinging at least two jets.

11. Dispensing device according to claim 1, wherein the inserts contain multiple different formulations, wherein the formulations are mixable only during dispensing.

12. Dispensing device according to claim 1, wherein the inserts are rotatable or movable in a direction in or out of the carrier, the direction being at least one of radial, tangential, axial and transversal to the moving or indexing direction of the carrier.

13. Dispensing device according to claim 1, wherein the dispensing device is at least one of an oral inhaler and a dry powder inhaler.

14. Dispensing device according to claim 1, wherein the insert contains a formulation formed of at least one of an anticholinergicum, a beta-sympathomimeticum, a steroid, a PDEIV-inhibitor, a LTD4-antagonist, an EGFR-kinase-inhibitor, and antiallergicum.

15. Dispensing device according to claim 1, wherein the storage chamber is substantially cylindrical, having a smooth contour without sharp edges or corners.

16. Method for dispensing a preferably medical formulation as a spray including fine particles from a storage device comprising multiple separate and pre-metered doses of the formulation, comprising the steps of:

storing the doses in multiple inserts in a carrier with each insert containing one dose of the formulation and being located in a separate sealed cavity of the carrier, individually opening the cavities for dispensing the respective dose from the respective insert by means of a piercing element, the piercing element piercing a sealing covering the respective cavity, following opening of the respective cavity, using the piercing element to pierce the respective insert and after the respective insert is pierced by the piercing element, supplying pressurized gas through the piercing element into the pierced insert to dispense the dose of formulation contained in the respective insert pierced.

17. Method according to claim 16, wherein the cavities are sealed by one or two common sealings.

18. Method according to claim 17, wherein each cavity is opened by pushing the respective insert at least partially out of the respective cavity.

19. Method according to claim 16, wherein each cavity is opened by pushing the respective insert at least partially through a respective sealing.

20. Method according to claim 16, wherein the respective insert is at least partially pushed out of the respective cavity by means of an abutment on the piercing element.

21. Method according to claim 16, wherein the piercing element is pushed through a sealing of at least one of the respective cavity and insert to connect the respective insert to the supply of pressurized gas.

22. Method according to claim 16, wherein the doses are individually subjected to a gas pressure for dispensing.

23. Method according to claim 22, wherein air is pressurized and used as the gas.

24. Method according to claim 16, wherein each dose is dispensed through a duct or nozzle of the respective insert.

25. Method according to claim 16, wherein the formulation is one of a liquid and a powder.

26. Method according to claim 16, wherein the formulation contains at least one of an anticholinergicum, a beta-sympathomimeticum, a steroid, a PDEIV-inhibitor, a LTD4-antagonist, an EGFR-ki-nase-inhibitor, and an antiallergicum.

* * * * *